US006955653B2

(12) United States Patent
Eggers

(10) Patent No.: US 6,955,653 B2
(45) Date of Patent: Oct. 18, 2005

(54) ELECTROSURGICAL METHOD AND APPARATUS WITH DENSE TISSUE RECOVERY CAPACITY

(75) Inventor: Philip E. Eggers, Dublin, OH (US)

(73) Assignee: Neothermia Corporation, Natick, MA (US)

( * ) Notice: Subject to any disclaimer, the term of this patent is extended or adjusted under 35 U.S.C. 154(b) by 84 days.

(21) Appl. No.: 10/630,336

(22) Filed: Jul. 30, 2003

(65) Prior Publication Data

US 2005/0027209 A1 Feb. 3, 2005

(51) Int. Cl.⁷ .............................................. A61B 10/00
(52) U.S. Cl. .................................. 600/564; 606/39
(58) Field of Search ...................... 600/562, 564–567; 606/34, 37–41, 45–50

(56) References Cited

U.S. PATENT DOCUMENTS

| | | | |
|---|---|---|---|
| 5,709,697 A | * | 1/1998 | Ratcliff et al. .............. 606/180 |
| 6,277,083 B1 | | 8/2001 | Eggers et al. |
| 6,471,659 B2 | | 10/2002 | Eggers et al. |
| 6,517,498 B1 | * | 2/2003 | Burbank et al. ............ 600/564 |
| 6,626,903 B2 | * | 9/2003 | McGuckin et al. ........... 606/45 |
| 6,740,079 B1 | * | 5/2004 | Eggers et al. ................. 606/34 |

OTHER PUBLICATIONS

Parker, Steve H. "The Advanced Breast Biopsy Instrumentation: Another Trojan Horse?" *Am. J. Radiology* 171: 61–53 (1998).

D'Angelo, Philip C., et al. "Stereotactic Excisional Breast Biopsies Utilizing the Advanced Breast Biopsy Instrumentation System" *Am J Surg.* 174: 297–302 (1997).
Ferzli, George S., et al. "Advanced Breast Biopsy Instrumentation: A Critique", *J Am Coll Surg.* 185: 145–151 (1997).
Rosen, Paul Peter, *Rosen's Breast Pathology*, Philadelphia: Lippincott–Raven Publishers, pp. 837–858 (1997).
Parker, Steve H., Needle,) *Percutaneous Breast Biopsy* Eds. Parker, et al, Raven Press, new York, pp 7–14 (1993.
Parker, Steve H. "Stereotactic Large–Core Breast Biopsy," *Percutaneous Breast Biopsy* Eds. Parker, et al, Raven Press, new York, pp. 61–79 (1993.

* cited by examiner

*Primary Examiner*—Charles Marmor
(74) *Attorney, Agent, or Firm*—Mueller and Smith, LPA

(57) ABSTRACT

Samples are recoverable from very dense tissue utilizing an instrument incorporating a capture component formed with leafs extending to leaf tip regions supporting a stainless steel pursing cable assembly. The cables of this assembly are electrosurgically excited to define a confronting leading edge and extend rearwardly to a terminator component. Motor drive is imparted to the capture component to deploy the leafs at a substantially constant initial angle of attack. During this procedure the terminator component is drawn forwardly by the cable until encountering a cable stop whereupon continued motor operation loads the cables in tension. By applying a preliminary loading tension to the cables before encountering the pursing cable stop, the angle of attack of the leaf tip region is gradually altered to lessen the development of lateral tissue induced forces against the leaf structures.

26 Claims, 12 Drawing Sheets

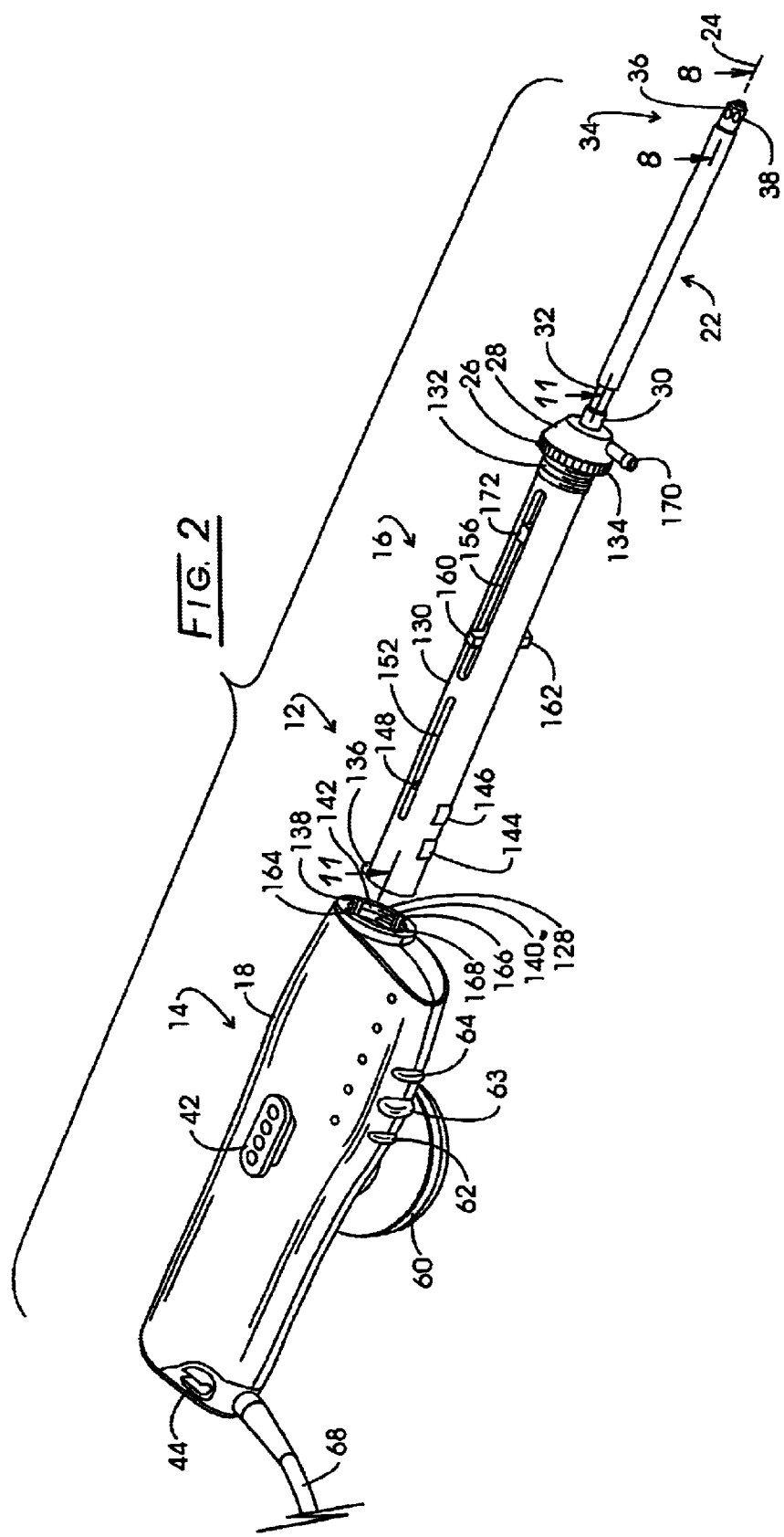

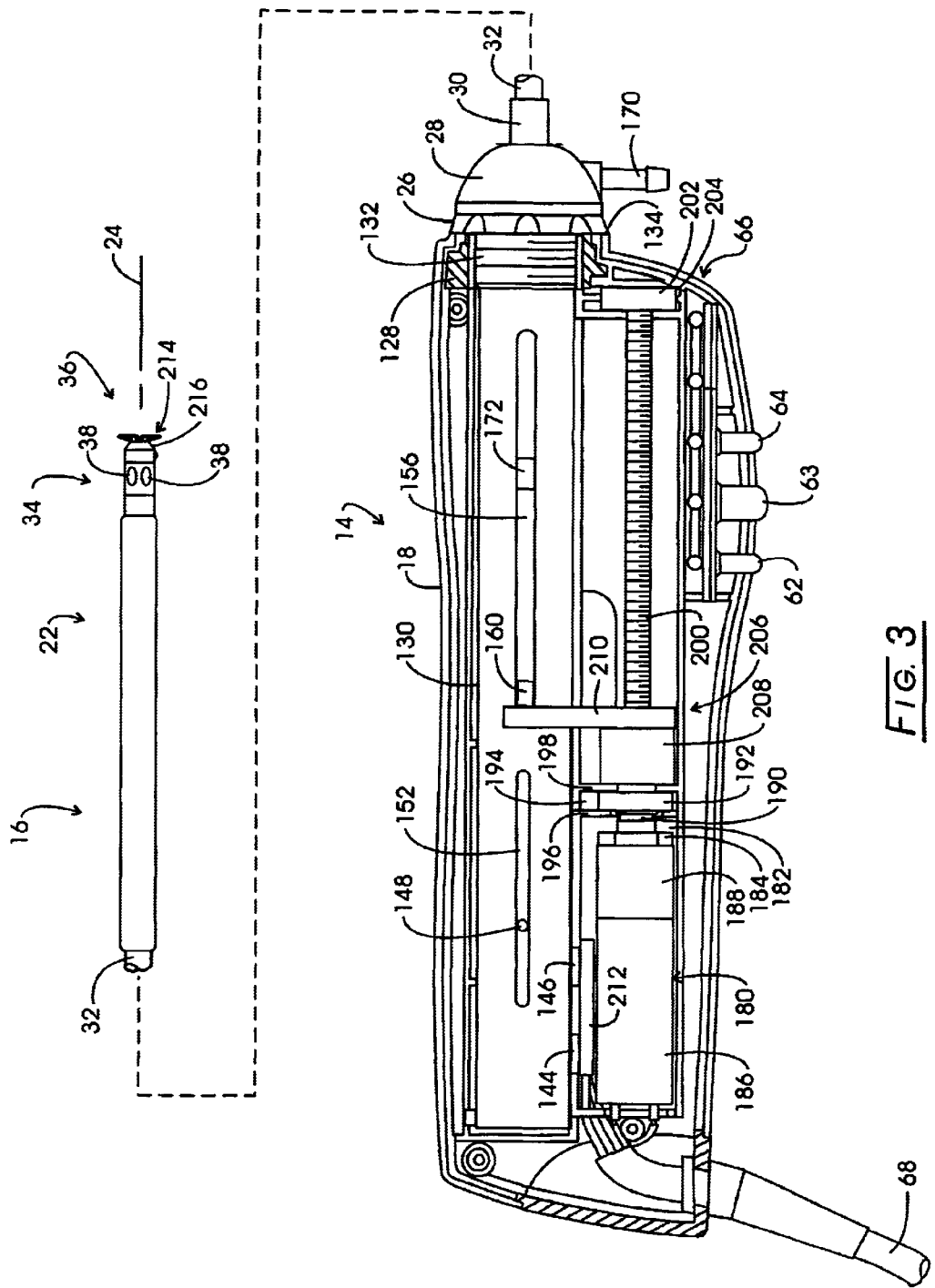

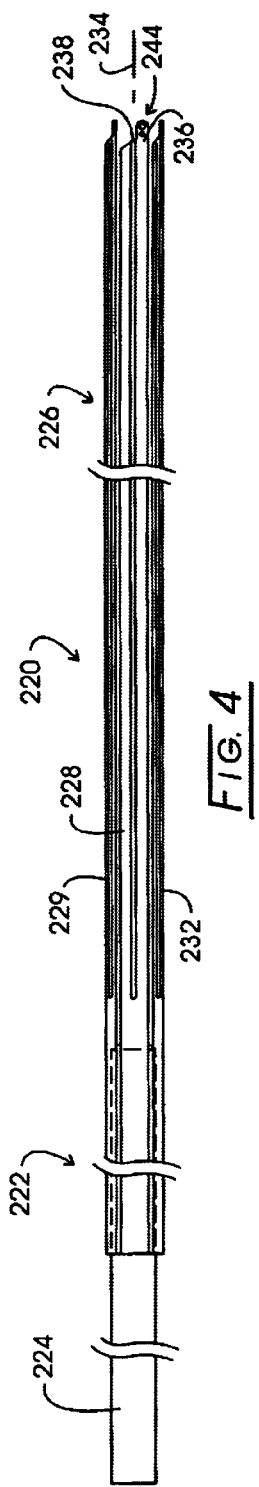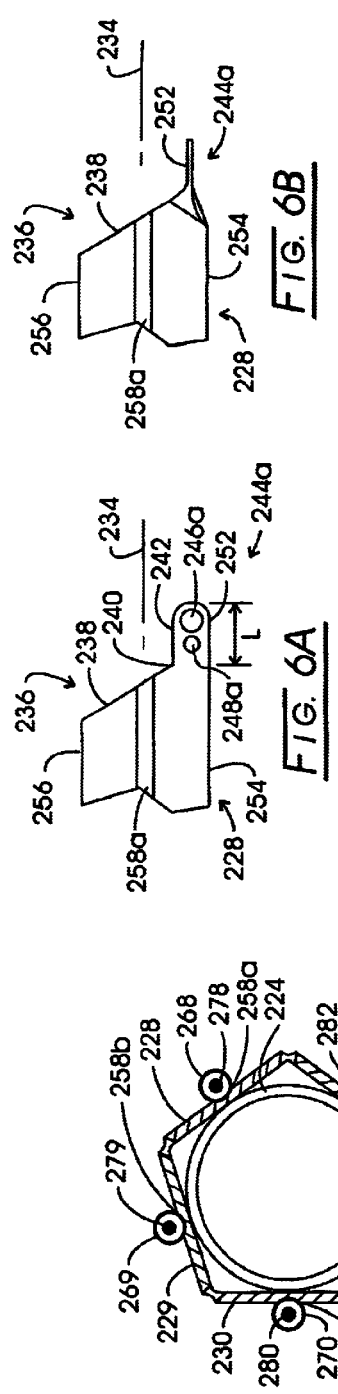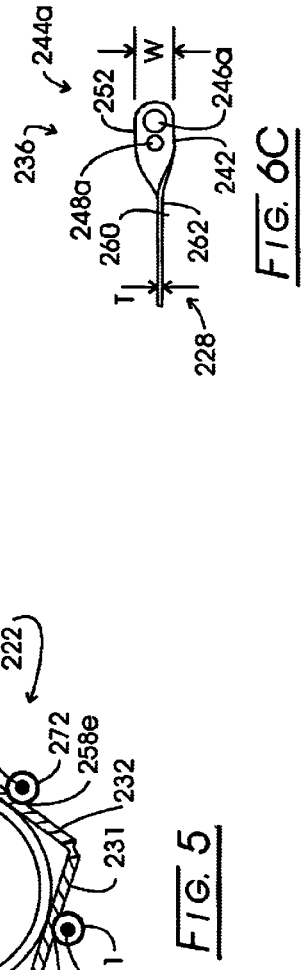

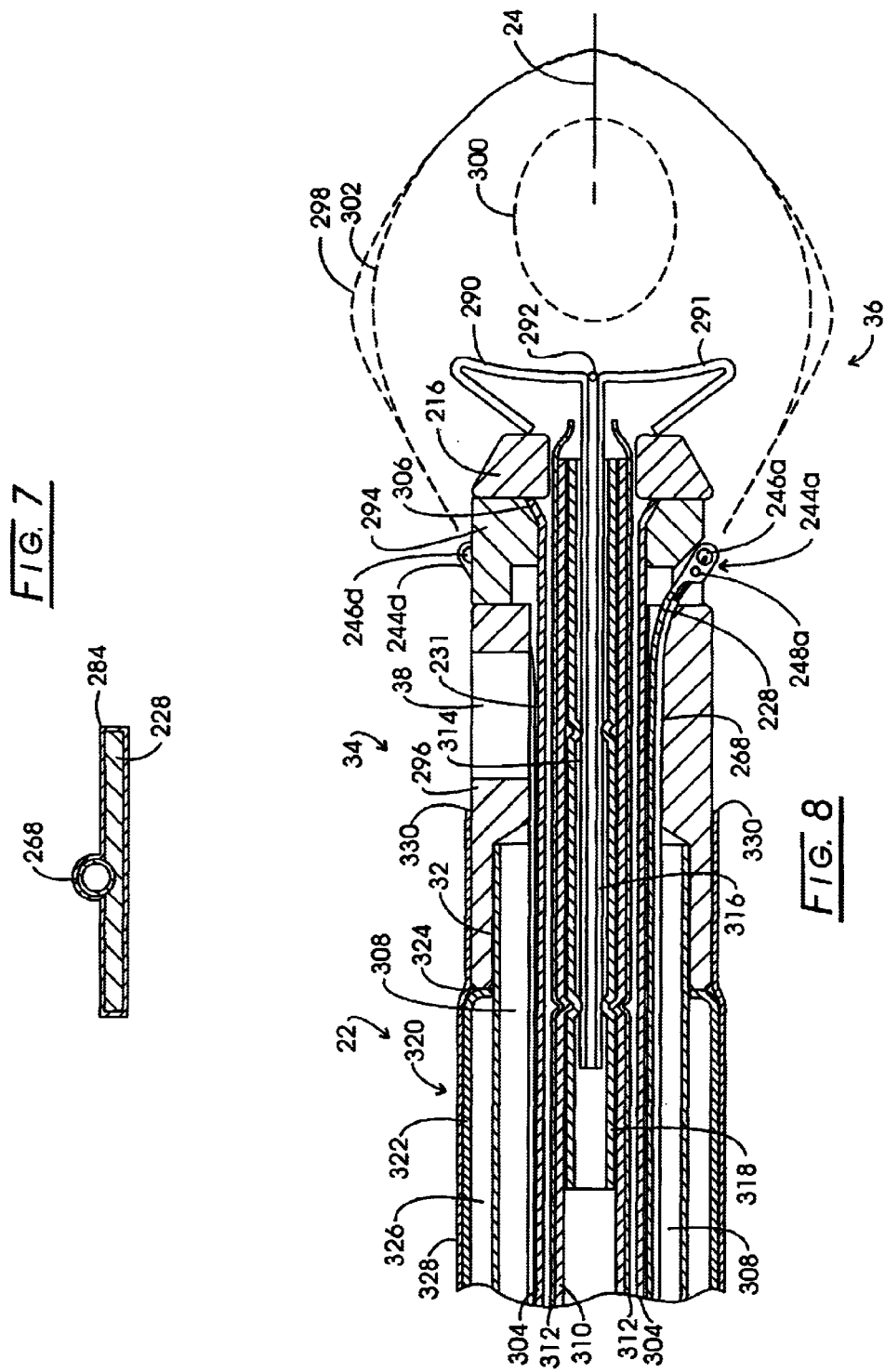

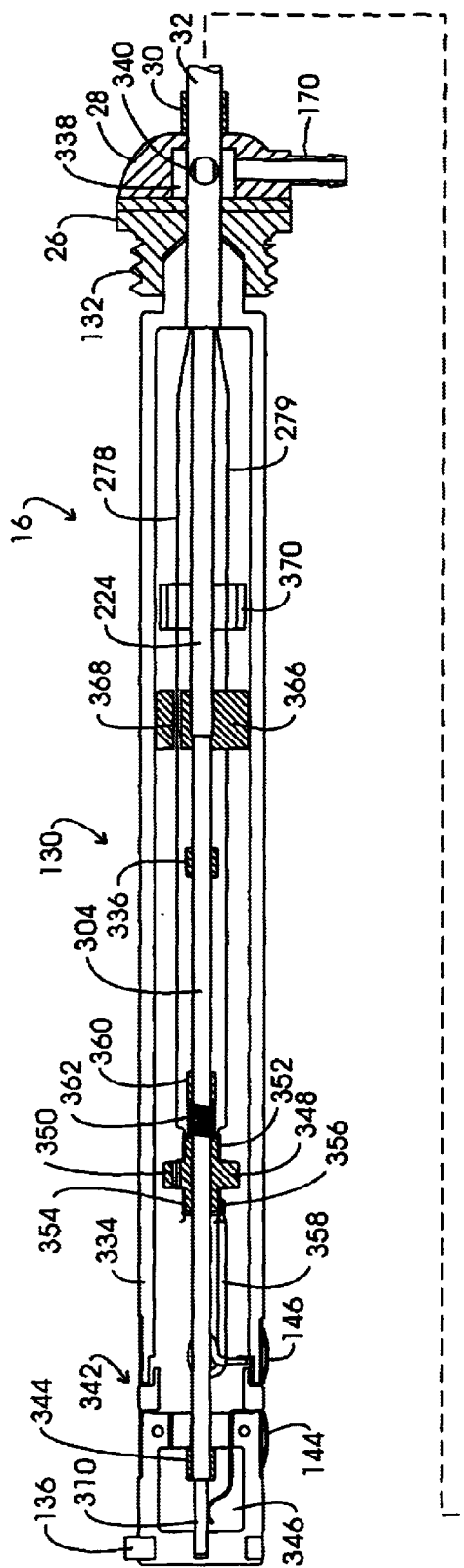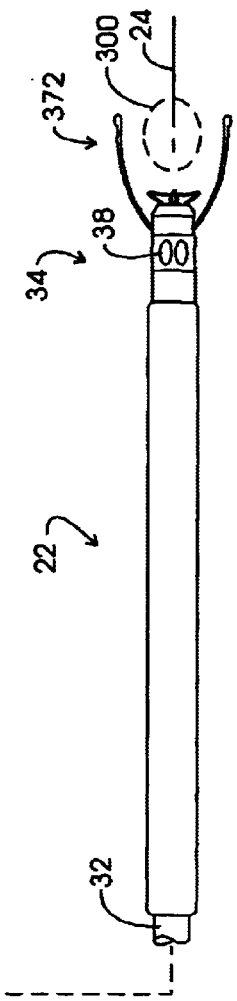
FIG. 12

TIME - (2)SECONDS

TIME - (2)SECONDS

ELECTROSURGICAL METHOD AND APPARATUS WITH DENSE TISSUE RECOVERY CAPACITY

CROSS-REFERENCE TO RELATED APPLICATIONS

STATEMENT REGARDING FEDERALLY SPONSORED RESEARCH

Not applicable.

BACKGROUND OF THE INVENTION

The detection of tumorous lesions in the breast has progressed from early observation and palpation procedures to a variety of somewhat sophisticated imaging systems. A consequence of these advances in tumor detection is the identification of suspect tumor at an early stage in its development. Generally, at such early stages the suspect tumor may be somewhat small. Rather than resort immediately to an open surgical resection upon such early detection, practitioners generally carry out a preliminary, minimally invasive biopsy procedure. Such preliminary biopsy approaches are of importance, inasmuch as statistically, only 20% of these small tumors will be found to be malignant. Tumors determined to be benign have been left in situ with no excision. Over one million of these biopsies are performed in the United States each year, the procedure providing for the removal of part or all the suspect tissue for pathology examination and diagnosis. See generally:

(1) Rosen, Paul Peter, "Rosen's Breast Pathology", Lippincott-Raven Publishers, Philadelphia, 1997 pp 837–858.

One of the minimally invasive options is needle biopsy which may be either fine needle aspiration (FNA) or large core. Fine needle aspiration (FNA) is a procedure in which a fine needle, for example, of 21 to 23 gauge, having one of a number of tip configurations, such as the Chiba, Franzeen or Turner, is inserted into the breast and guided to the tumor site. A vacuum is created and the needle moved up and down along the tumor to assure that it collects targeted cellular material. Generally, three or more passes will be made to assure the collection of sufficient sample. Then, the needle and tissue sample are withdrawn from the breast for analysis.

The resulting specimen is subject to cytologic assay. In this regard, cell structure and related aspects are studied. This analysis has been used to improve or customize the selection of chemotherapeutic agents with respect to a particular patient.

While a fine needle aspiration biopsy has the advantage of being relatively simple, there are some drawbacks associated with its use. With fine needle aspiration, there remains a risk of false-negative results, which most often occur in cases involving extremely fibrotic tumor. In addition, after the procedure has been performed there may be insufficient specimen material for diagnosis. Finally, with fine needle aspiration alone the entire area of suspect tissue is not removed. Rather fragmented portions of tissue are withdrawn which do not allow a more advanced pathological investigation.

This limitation also is observed with respect to large core needle biopsies. For a large core needle biopsy, a 14 to 18 gauge needle is inserted in the breast having an inner trocar with a sample notch at the distal end and an outer cutting cannula. Similar to a fine needle aspiration, tissue is drawn through a needle by vacuum suction. These needles have been combined with biopsy guns to provide automated insertion that makes the procedure shorter and partially eliminates location mistakes caused by human error or lesion displacement. Once inserted, multiple contiguous tissue samples may be taken at a time.

Samples taken during large core needle biopsies may be anywhere from friable and fragmented to large pieces 20 to 30 mm long. These samples may provide some histological data, unlike fine needle aspiration samples. However, they still do not provide optimum pathological information. For further information concerning needle biopsy procedures see the following:

(2) Parker, Steve H, "Needle Selection and Steriotatic Large-Core Breast Biopsy", *Percutaneous Breast Biopsy* Eds. Parker, et al, Raven Press, New York, 1993 pp 7–14 and 61–79.

A device, which is somewhere between a needle biopsy and open surgery, is referred to as the Advanced Breast Biopsy Instrumentation (ABBI). With the ABBI procedure, the practitioner, guided by appropriate imaging, removes a core tissue sample of 5 mm to 20 mm in diameter. While the ABBI has the advantage of providing a large tissue sample similar to that obtained from an open surgical biopsy, the cylindrical tissue sample is taken from the subcutaneous tissue to an area beyond the suspect tumor. For tumors embedded more deeply within the breast, the amount of tissue removed is considerable. In addition, while less expensive than open surgical biopsy, the ABBI has proven expensive compared to other biopsy techniques, and it has been noted that the patient selection for ABBI is limited by the size and location of the tumor, as well as by the presence of very dense parenchyma around the tumor. See the following publications:

(3) Parker, Steve H., "The Advanced Breast Biopsy Instrumentation: Another Trojan Horse?", Am. J. Radiology 1998; 171:51–53.

(4) D'Angelo, Philip C., et al., "Sterotatic Excisional Breast Biopsies Utilizing The Advanced Breast Biopsy Instrumentation System", Am. J. Surg. 1997; 174: 297–302.

(5) Ferzli, George S., et al., "Advanced Breast Biopsy Instrumentation: A Critique", J. Am. Coll. Surg., 1997; 185: 145–151.

Another biopsy approach has been referred to as the mammotome and the Minimally Invasive Breast Biopsy (MIBB). These devices carry out a vacuum-assisted core biopsy wherein fragments of suspect tissue are removed with an 11–14 gauge needle. While being less invasive, the mammotome and MIBB yield only a fragmentary specimen for pathological study. These devices therefore are consistent with other breast biopsy devices in that the degree of invasiveness of the procedure necessarily is counterbalanced against the need of obtaining a tissue sample whose size and margins are commensurate with pathology requirements for diagnosis and treatment.

A minimally invasive approach to accessing breast lesions wherein the lesion is partially removed or removed in its entirety for diagnostic as well as therapeutic purposes has been described in U.S. Pat. No. 6,277,083 by Eggers, et al., entitled "Minimally Invasive Intact Recovery Of Tissue", issued Aug. 21, 2001. The instrument described includes a tubular delivery cannula of minimum outer diameter, the tip of which is positioned in confronting adjacency with a tissue volume to be removed. Following such positioning, the electrosurgically excited leading edge of a capture component is extended forwardly from the instrument tip to enlarge while electrosurgically cutting and surrounding or encapsulating a tissue volume, severing it from adjacent tissue. Following such capture, the instrument and the encaptured tissue volume are removed through an incision of somewhat limited extent.

An improved design for this instrument, now marketed under the trade designation EN-BLOC® by Neothemia Corporation of Natick Massachusetts, is described in U.S. Pat. No. 6,471,659 by Eggers, et al., entitled "Minimally Invasive Intact Recovery Of Tissue", issued Oct. 29, 2002. The EN-BLOC® instrumentation includes a tubular delivery cannula of minimum outer diameter, the tip of which is positioned in confronting adjacency with the target tissue volume to be removed. Such positioning is facilitated through the utilization of a forwardly disposed precursor electrosurgical electrode assembly. Located within the interior channel of this delivery cannula is a capture component configured with five relatively elongate and thin leafs which are mutually interconnected at their base to define a pentagonal cross-sectional configuration. Each of these leafs terminates forwardly at a tip region with a transversely bent forwardly extending eyelet structure. Slidably extending through each eyelet is an electrically conductive pursing cable of a pursing cable assembly. The tips additionally extend through a guidance assembly at the forward region of the delivery cannula. When the capture component is driven forwardly by the drive tube of a drive assembly, these leafs deploy outwardly and forwardly at an initial angle of attack of 35° to 45° while the pursing cables are "played out" and establish an electrosurgical cutting arc. Thus, cable movement defines a cutting profile that is extending outwardly at the noted 35° to 45° while moving forwardly to define an initial cutting profile extending circumferentially about the targeted tissue volume.

Drive imparted to the capture component from the drive tube is developed ultimately from an electric motor within the drive assembly. Each of the five pursing cables extends from the leading edge portion of the capture component through the delivery cannula to a cable terminator component which is pulled forwardly by the cable as the capture component forward portion moves from its initial position substantially within the interior channel of the delivery cannula toward an intermediate position wherein the electrosurgically excited leading edge leaf forward regions and associated pursing cables have achieved an effective maximum diametric extent. At this juncture, about one half of the targeted tissue volume will have been circumscribed by the capture component. At this position, the slidable cable terminator component will engage a cable stop component or collar. Forward movement of the attached cable assembly will be halted and a pursing action will ensue at the electrosurgical cutting leading edge wherein the tip regions of the cables are drawn inwardly with mutually inwardly directed angles of attack until the leaf tip portions converge at a capture position defining a capture basket configuration or tissue recovery cage substantially encapsulating the entire target tissue volume. As this position is reached, the tensioned cables permit no further movement and a stall condition is recognized at the drive motor to terminate electrosurgical excitation of the cable-defined leading edge of the capture component. Drive then is removed from the capture component by reversing the directional output of the electric motor.

An advantageous feature of this form of drive assembly for the capture component resides in an arrangement where the noted cable stop component which engages the cable terminator component may be adjusted longitudinally to, in turn, vary the extent of the effective maximum diameter developed by the leading edge of the capture component. For example, the device can be configured to recover tissue specimens of 10 mm, 15 mm, 20 mm or greater effective maximum diametric extent. With the system, capture is positive, minimally invasive and the procedure is of short duration, for instance, requiring about 7 seconds to recover a 10 mm maximum effective diameter tissue sample. As another beneficial aspect, the shape of the resultant specimen is compact in that it will exhibit an aspect ratio of from about 1:1 to about 1:1.5 of effective diametric extent to longitudinal length. This is achieved by the initial 35° to 45° angle of attack of deployment to the intermediate position and the utilization of one pursing cable per leaf to essentially define a spherical encapsulation. In this regard, where stereotactic guidance and imagining is employed, the breast will be engaged with a compression plate such that recovery of elongate-shaped samples is undesirable.

Studies have been undertaken with respect to the employment of this instrument in the recovery of target tissue samples from very dense breast tissue including fibrous tissue. Such tissue will be infrequently encountered, however, a capability on the part of the instrument to recover samples from it is desirable. To emulate the dense tissue, porcine breast tissue was compressed with a clamping procedure. This provided a test medium which reproduced at least the mechanical properties of dense human breast tissue. The studies indicated that as the capture component leading edge reached the noted maximum effective diametric extent at its intermediate position or slightly beyond representing about a 50% to about a 75% deployment of the system, the system exhibited excessive motor currents which may reach levels indicating a stall characteristic. As the cable terminator engaged the maximum effective diameter defining cable stop to halt forward movement of the cables, their resultant stress load created these excessive motor currents which, in some cases, exceeded the control threshold representing a completion of capture. This potential capture failure phenomenon was observed to occur more frequently as the size of the maximum effective diameter increased, for instance, from 10 mm to 15 mm and above. However, the mechanical integrity of the capture component with pursing cables remained intact. While, as described in U.S. Pat. No. 6,471,659 (supra) the control system employs electronic masking to avoid shut-down due to frictional vagaries during early stages of the capture procedure, extension of such masking was deemed to be undesirable for safety-related reasons.

BRIEF SUMMARY OF THE INVENTION

The present invention is directed to tissue recovery apparatus system and method having the capability of electrosurgically recovering tissue samples from within very dense tissue. Tissue retrieval is carried out with an instrument incorporating a capture component fashioned with a plurality of thin, elongate leafs which extend from a base portion to tip regions having forwardly depending eyelet structures. A pursing cable assembly configured with a plurality of electrosurgically energizable stainless steel cables is supported at the eyelets to establish a cutting leading edge. These cables extend rearwardly to connection with a slidable cable terminator.

In its general operation, the capture component is motor driven forwardly from an initial retracted orientation, the leaf tip regions are deployed forwardly and outwardly at an initial, substantially unchanging angle of attack. Such attack may range from about 35° to 45° with respect to the longitudinal axis of the instrument. As the deployment movement progresses, the pursing cables are electrosurgically excited to create a cutting arc at the leading portions of the assembly. When the leading cables and associated leaf tip regions have extended to an intermediate position, they will define a confronting cutting profile of maximum effective diametric extent. At this juncture, the cable drawn terminator component will abuttably engage a capture stop, the location of which defines the maximum effective diameter of the confronting cutting profile. Blocked from movement, cables then are loaded in tension by the motor drive and the leaf tip regions are rapidly pursed to mutually converge to a capture orientation defining a tissue capture cage.

This tissue capture technique is made available for the retrieval of specimens from very dense tissue with the approach of providing a modulated pre-tension of the cables as the leaf tip regions approach the noted intermediate position. With this graduated tensional loading of the cables prior to the engagement of the terminator component with the capture stop, the angle of attack at the leaf tip region alters progressively from its initial angle of attack toward the axis of the instrument, until the terminator component movement is blocked to commence full pursing activity.

Such modulated pre-tensioning is achieved by applying a gradually retarding spring bias against forward movement of the terminator component. The resilient member or spring required will exhibit mechanical characteristics which are pertinent to the maximum effective diameter of capture. Where the spring or springs utilized are compression springs, their length also is determined with respect to that maximum effective capture diameter. For instance, where the maximum effective capture diameter extends from about 10 mm to about 15 mm, a compression spring exhibiting a spring rate of about 7 to 10 pounds per inch and a length of about 0.25 inch is called for. In contrast, where the maximum effective diameter of about 20 mm is at hand, then a compression spring exhibiting a spring rate of about 10 to 15 pounds per inch and a length of about 0.25 inch is called for.

Other features and objects of the invention is to provide a method for isolating and retrieving a tissue volume, comprising the steps of:

(a) providing a delivery member having an interior channel extending from a proximal portion along the longitudinal axis to a forward region having a distal end;

(b) providing a capture component positioned at the delivery member forward region, having a forward portion comprised of a plurality of cable supports having tip portions of given width supporting a forwardly disposed pursing cable assembly including one or more electrically conductive tensionable cables extending from the tip portions along the interior channel and arranged at the tip portions to define an electrosurgical cutting edge, the forward portion having an initial position substantially within the interior channel;

(c) positioning the delivery member at an operative location wherein the distal end is located in adjacency with the tissue volume;

(d) electrosurgically exciting the capture component cables to form a cutting arc at the electrosurgical cutting edge;

(e) driving the capture component from the initial position to effect the deployment of the cable supports at an initial angle of attack and to expansively move the electrosurgical cutting edge toward an intermediate position corresponding with a cutting profile defining a maximum effective diametric extent;

(f) loading the cables with a pursing stress which progressively increases to progressively alter the angle of attack of the cable support tip portions defining a curvature toward the longitudinal axis as the intermediate position is approached to an extent facilitating the forward movement of the cable support;

(g) loading the cables with a pursing value of tensile stress effective to converge the tip portions to a capture position defining a tissue recovery cage substantially encapsulating the tissue volume;

(h) terminating the electrosurgical excitation; and (i) removing the delivery member forward region from the operative location.

Other objects of the invention will, in part, be obvious and will, in part, appear hereinafter. The invention, accordingly, comprises the system, method and apparatus possessing the construction, combination of elements, arrangement of parts in steps which are exemplified in the following detailed description.

For a fuller understanding of the nature and objects of the invention, reference should be made to the following detailed description taken in connection with the accompanying drawings.

BRIEF DESCRIPTION OF THE DRAWINGS

FIG. 2 is an exploded view of an electrosurgical instrument shown in FIG. 1;

FIG. 3 is a partial sectional view of the instrument shown in FIG. 2 with portions broken away;

FIG. 4 is a side view showing a capture component employed with the instrument of the invention illustrating its structure at a stage of production;

FIG. 5 is a sectional view of a completed capture component;

FIG. 6A is a plan view of the forward region of a leaf of the capture component of FIG. 4 illustrating its structure at a stage of production;

FIG. 6B is a plan view of the forward tip region of the leaf shown in FIG. 6A but with its eyelet structure twisted to perpendicularity with respect to a leaf face;

FIG. 6C is a side view of the tip region shown in FIG. 6B;

FIG. 7 is a sectional view of a leaf of a capture component employed with the invention;

FIG. 8 is a partial sectional view of the forward region of the disposable component of the instrument of FIG. 2;

FIG. 12 is a partial sectional view of the instrument of FIG. 11 showing the orientation of components at a deployment of a capture component to a maximum diametric extent;

DETAILED DESCRIPTION OF THE INVENTION

In the discourse to follow, the above-noted EN-BLOC® system is described in order to facilitate an understanding of how it is mechanically or physically affected when encountering very dense tissue, as well as how the control components may react to such phenomenon. As the description unfolds, features which assure successful utilization of the system with this type tissue are detailed.

Figure 1:
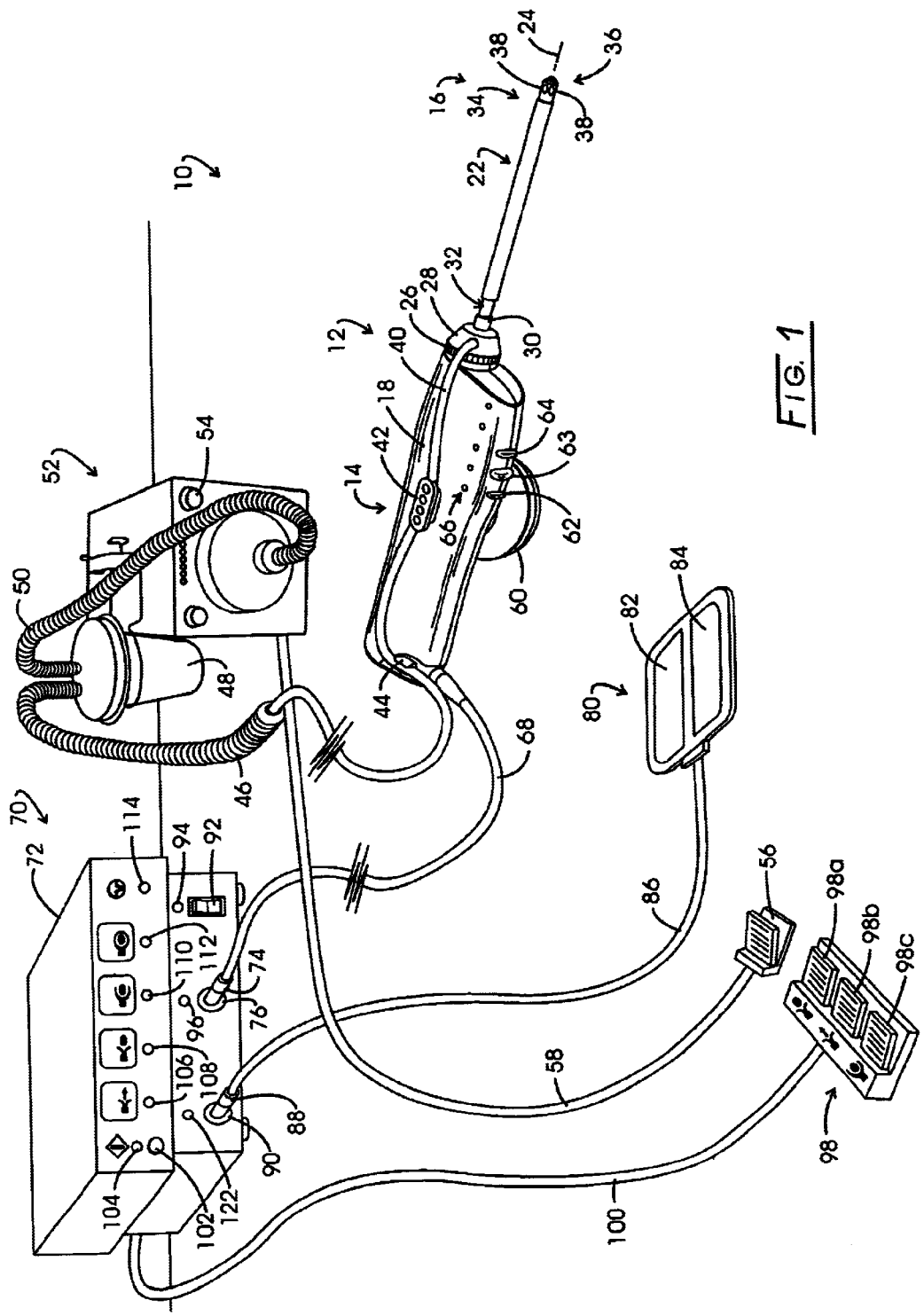
FIG. 1 is a perspective view of an electrosurgical system according to the invention.

Referring to FIG. 1, the noted system for isolating and retrieving a target tissue volume or biopsy sample is illustrated in general at 10. System 10 comprises a tissue retrieval instrument represented generally at 12 which includes a reusable component represented generally at 14, sometimes referred to as a "handle". Instrument 12 additionally includes a disposable component represented generally at 16, the rearward portion of which is removably mounted within the polymeric housing 18 of reusable component 14. The disposable component 16 is sometimes referred to as a "probe".

Disposable component 16 includes an elongate cannula assembly or delivery member represented generally at 22 which extends along an instrument axis 24. The proximal end of cannula assembly 22 extends through a rotatable, externally threaded connector 26. Connector 26, in turn, is threadably engaged within housing 18. Cannula assembly 22 additionally extends through a rotatable suction manifold 28 which is a component of an evacuation system. Manifold 28 is retained in position on cannula assembly 22 by a ferrule or collar 30 which is mounted over the outward surface of a tubular cannula component, a portion of which is represented at 32. Most of the outward surface of the cannula assembly 22 will be seen to be covered with an electrically insulative thin polyolefin shrink-wrap or tube. The forward region of the cannula assembly 22, as represented generally at 34 extends to a distal end or tip represented generally at 36. Suction or vacuum manifold 28 is in vacuum conveying and fluid receiving relationship through cannula assembly 22 with four intake ports located at forward region 34, two of which are shown at 38. The evacuated fluids will be at an elevated temperature due to the electrosurgical nature of the instrument 12 and will include steam, smoke and liquid such as blood and accumulations of local anesthetic. Vacuum is conveyed to and this noted elevated temperature fluid is received from suction manifold 28 via a flexible transparent polymeric tube 40. Tube 40 extends from an evacuation outlet (not shown) at manifold 28 into press-fit connection with connectors 42 and 44, whereupon it is coupled with a flexible tube or hose of larger diametric extent shown at 46. Hose 46 extends to a fluid trap and filter assemblage 48 which is in vacuum communication via flexible hose 50 with the suction input of a suction pump assembly represented generally at 52. Vacuum or suction pump assembly 52 may be of a type marketed under the trade designation "VersaVac 2" by Stackhouse, Inc. of Palm Springs, Calif. Pump assembly 52 may be actuated into operation from a switch arrangement shown at 54 or through the utilization of a footswitch 56 coupled to the pump assembly 52 via a cable 58.

Connectors as at 42 are positioned on each side of the housing 18 and function additionally to support a stabilizer handgrip, for example, the annulus-shaped grip represented at 60. Connectors as at 42 also may be employed to support the instrument 12 for stereotactic manipulation. Positioned at the forward portion of the housing 18 are three button switches 62–64 which function respectively as an arm/disarm switch; an energize/position switch; and a start tissue capture switch. Immediately above the switches 62–64 on each side of housing 18 are linear arrays of light emitting diode (LED) based indicator or cueing lights, one such array being represented generally at 66. The visual cues provided by the indicators at array 66, from the forward region of housing 18 toward the rear region thereof, provide a start/reset cue as a green light; a tissue capture complete cue provided as a green light; a start tissue capture cue (above switch 64) provided as a yellow light; an energize/position cue (above switch 63) provided as a yellow light; and an arm/disarm cue (above switch 62) provided as a green light. Energization and electrical control is provided to the instrument 12 via a multi-lead cable 68 which connects with a combined control assembly and electrosurgical generator represented generally at 70 and incorporated within a console 72. The control assembly function performs in conjunction with control assembly counterparts incorporated within instrument 12 and principally within reusuable component 14. Device 70 is provided as a model "3000 RF Controller" marketed by Neothermia Corporation (supra). Connection of the cable 68 with the console 72 is shown at a multi-lead connector 74 which is coupled to a console connector 76. The electrosurgically active electrode assembly of the instrument 12 performs in monopolar fashion. Thus, a conventional, relatively large, dispersive return electrode assembly, as shown in general at 80, is positioned against the skin surface of the patient. Assembly 80 is configured as having two electrode components 82 and 84 which are connected via cable 86 and connector 88 to console connector 90. Alternately, a return electrode may be positioned at the surface of cannula assembly 22 near its distal end in place of the illustrated use of a dispersive return 80.

Power is supplied to the circuitry at console 72 upon actuation of an on/off switch 92. When switch 92 is in an "on" orientation, a green visual indicator LED 94 located above the switch is energized. Proper connection of the cable 68 and connector 74 with console connector 76 is indicated by an illuminated green LED 96 positioned above connector 76. This connection test is carried out by directing current to a coding resistor within housing 18. A three-pedal footswitch represented generally at 98 is coupled via a cable 100 to the rear panel of console 72. The three pedals, 98a–98c of switch 98 emulate and provide alternative switching with respect to button switches 62–64.

Visual cueing corresponding with that at housing 18 LED arrays as at 66 also is provided at the console 72. In this regard, a start/reset switch 102 is operationally associated with an LED indicator 104 which illuminates in a green color upon actuation of that switch. An energize/position mode visual cue LED representing an energization of a precursor electrode assembly at tip 36 is shown at 106. This LED provides a yellow output during the electrosurgical advancement of cannula assembly tip 36 into confronting adjacency with a targeted tissue volume. Next, a green, arm/capture mode visual cue is provided by an LED 108 to represent an arming of the tissue capture feature of instrument 12. Once an arm/disarm switch as at 62 or 98a is depressed, the energize/position switches as at 63 or 98b are no longer activatable. However, the practitioner may return to the positioning mode by again depressing an arm/disarm switch. To enter the capture mode, the practitioner depresses footswitch 98c or capture switch 64. A yellow capture mode visual cue is provided by an LED 110 to represent the start of and carrying out of a tissue capture or retrieval procedure and upon completion of such capture, a green capture complete visual cue is provided by a green LED 112. A pause mode condition is represented by the energization of a green LED 114. In general, the pause mode is entered during a procedure by releasing capture switch 64 or footswitch 98c. When in a pause mode, the active capture electrodes of the instrument 12 are not energized and deployment of its capture component is halted. However, the evacuation function carried out by the suction pump assembly 52 continues to perform. To reenter the capture mode, the practitioner again depresses footswitch 98c or capture switch 64. Upon such re-actuation of the chosen switch, the capture mode continues, in effect, from the orientation where it left off. This pause mode of operation of the system may be employed by the practitioner during a capture mode of operation to permit, for example, the evacuation of fluids encountered by arc-based cutting components. Such fluids may, for example, be accumulations of local anesthetic solution, blood or the like.

An assurance that the vacuum system is operating, at least to the extent that the vacuum pump assembly 52 is active, can be accomplished with a vacuum actuated switch (not shown) attached with the conduiting extending between the pump assembly 52 and the instrument 12. For example, unless such a switch is actuated, the commencement of a procedure can be logically blocked by the control assembly 70. In addition to the removal of smoke and such fluids as are discussed above, the evacuation system including pump assembly 52, conduiting defining a transfer channel extending to the intake ports 38, functions to remove steam which is generated by the encounter of an electrosurgical cutting arc with fluid of tissue cells. This removal of steam (as a component of elevated temperature fluid) serves, inter alia, to protect healthy tissue surrounding the region of cutting from thermal trauma.

At the time the connector 88 of return electrode 80 is coupled to console connector 90 and switch 92 is in a power-on condition, a patient circuit safety monitor (PCSM) carries out a self test. On subsequent actuation of the start/reset switch 102, a fault test with respect to the two electrode components 82 and 84 is performed. In the event the latter test fails, then both visual and aural pulsating warning cues are activated, the visual cue being provided at a red LED 122 located adjacent connector 90.

Referring to FIG. 2, the disposable component 16 of instrument 12 is revealed in an orientation prior to its insertion within the housing 18 of reusable component 14. In the figure, cannula assembly 22 is seen extending forwardly from a cylindrically-shaped support housing 130. The forward region of support housing 130 supports the rotatable connector 26. In this regard, it may be observed that the connector 26 is configured with external threads 132 which are affixed for rotation with a grasping surface 134 formed with spaced indentations to facilitate its hand rotation. At the rearward end of support housing 130 there is located an upstanding indexing pin 136 which, during installation of the disposable component 16, is slidably received within an upwardly disposed elongate slot 138 extending internally along an elongate receiving cavity 140. The forward end of receiving cavity 140 of housing 18 is formed by alignment bushing 128. Alignment bushing 128 is formed with internal threads 142. Internal threads 142 of alignment bushing 128 within cavity 140 threadably engage the external threads 132 of connector 26 when the disposable component 16 is mounted with the reusable component 14.

Positioned opposite indexing pin 136 on support housing 130 are two, spaced apart electrical contacts 144 and 146 which are oriented to make wiping contact with corresponding electrical terminals disposed within housing 18 upon insertion of support housing within the receiving cavity 140. Contacts 144 and 146 selectively receive electrosurgical cutting current which is applied respectively to a precursor electrode assembly at tip 36 and the electrosurgical cutting and pursing cables associated with a capture component initially retained within cannula assembly 22. Those pursing cables extend from the capture component within cannula component 32 to a cable terminator component having guidance tabs or ears, one of which is revealed at 148 slidably mounted within an elongate stabilizer slot 152 arranged in parallel with axis 24. A corresponding guidance tab and slot combination is found at the opposite side of support housing 130. Located forwardly of the slots as at 152 are two elongate drive slots, one of which is shown at 156 similarly arranged in parallel with axis 24. The outwardly extending ears or guide tabs of a drive assembly drive member extend from these slots and are seen at 160 and 162. These ears or tabs 160 and 162 support rearwardly disposed driven surfaces which are used to impart forward movement to the drive assembly components. This forward movement functions to deploy the noted capture component from cannula component 32. When the support housing 130 is installed within the receiving cavity 140 of housing 18, these tabs 160 and 162 pass through oppositely disposed notches shown respectively at 164 and 166 provided at a forward portion of housing 18 as part of alignment bushing 128. Similarly, a notch 168 is located forwardly within housing 18 to permit passage of the electrical terminals 144 and 146. Alignment bushing 128 is configured to form the forward portion of elongate slot 138 and notch 168.

The procedure for installing the disposable component 16 within reusable component 14 involves the sliding of support housing 130 within the receiving cavity 140 and rotating grasping surface 134 of connector 26 to provide for the engagement of threads 132 with threads 142. Upon completing the assembly, the flexible transparent tube 40 of the evacuation assembly may be attached to an evacuation outlet 170 depending outwardly and in fluid and suction or vacuum communication with suction manifold 28. Finally, a tab as at 172 is seen extended through a forward portion of the drive slot 156. This tab may be a component of a drive assembly safety stop functioning to limit the extent of forward travel permitted by the drive member component having the ears 160 and 162. It is located in accordance with a pre-selected capture component maximum effective diametric extent.

Such a tab also may function as a capture complete stop which serves in the derivation of a capture complete signal derived as the current spike witnessed upon a stall of an electric drive motor. That signal is conveyed to control assembly 70.

Referring to FIG. 3, a sectional view is presented illustrating the operative association of motor drive features of the reusable component 14 with the support housing 130 of disposable component 16. In the figure, a motor assembly represented generally at 180 is seen to be located within a motor mount chamber 182. In that chamber 182 the motor assembly 180 is permitted some self-aligning movement but is restrained from rotational movement by a torque stop component 184. Motor assembly 180 incorporates a motor component 186 which is coupled in driving relationship with a planetary gear assembly 188. The drive output of the planetary gear assembly 188 is connected in driving relationship with a stainless steel flexible bellows-shaped coupler 190 which extends through a fluid seal 192 located within a seal chamber 194 defined by oppositely disposed and spaced apart bulkheads 196 and 198. Seal 192 does not constrain the coupler 190 and permits the noted self-alignment of motor assembly 180 with respect to its coupling to a rearward end of an elongate threaded translation component 200. The forward end of translation component 200 extends into engagement with a thrust bearing 202. Bearing 202 provides support against all of the driving forces imposed from the motor assembly 180 and is mounted and secured within a thrust bearing chamber 204. Translation component 200 is threadably engaged with a transfer assembly represented generally at 206 which comprises a ball screw or nut component 208 and a generally Y-shaped yoke 210 which is configured to extend to a position aligned for driving but freely abutting engagement with the tabs or ears 160 and 162 (FIG. 2). During a capture procedure, the translation component 200 is drivably rotated in an appropriate direction to move the transfer assembly 206 forwardly. That movement, in turn, urges a drive component forwardly until capture component pursing activity is completed and the motor component 186 enters a stall condition. At that juncture, the control system 70 halts electrosurgical cutting current and reverses the directional drive sense of motor 186 to cause the transfer assembly 206 to return to a "home" position generally illustrated in the instant figure. The figure additionally reveals that the two electrical contacts 144 and 146 located upon support housing 130 will be in contact with corresponding contacts (not shown) supported by a polymeric contact clamp 212.

FIG. 3 also reveals some details of the tip 36 of the cannula assembly 22. The tip incorporates four precursor electrode components arranged in a cross-shape or symmetrically about instrument axis 24 as is represented in general at 214. These precursor electrodes are located just forwardly of a truncated cone-shaped ceramic (alumina) protective tip component 216. Tip component 216 functions to provide an arc-resistant or arc isolating tip portion preventing its breakdown.

A more detailed description of the system 10 including the control assembly 70 and the drive system within housing 18 is provided in the above-referenced U.S. Pat. No. 6,471,659 which is incorporated herein by reference.

The forward drive movement of transfer assembly 206 by motor assembly 180 and translation component 200 serves to impart forward drive to a drive member within cylindrical support housing 130 which, in turn, drives forwardly a drive tube functioning to deploy a capture component, the leading edge of which is provided as a pursing cable assembly having an initially expanding and then contracting effective diametric extent which circumspectively cuts around the target tissue volume and thus isolates and encapsulates a resultant tissue sample for removal.

Referring to FIG. 4, this capture component which is retained within the internal structure of cannula component 32 prior to its deployment is represented in general at 220 at a stage in its fabrication prior to the attachment of pursing cables and associated polymeric guide tubes for those cables. Component 220 is formed by chemically milling flat type 304 stainless steel sheet stock to provide for the formation of a pentagonal base portion represented generally at 222 which is weldably attached to the above-noted drive tube represented at 224. Drive tube 224 extends through the cannula component 32 and into the interior of cylindrical housing 130 (FIG. 2). Formed integrally with the base portion is a leaf assembly represented generally at 226. Looking additionally to FIG. 5, the sleeve assembly is seen to be comprised of leafs 228–232, a bending notch being chemically milled to define these leafs within the base portion 222 and each leaf having a chemically milled groove extending along its centrally disposed leaf axis. Such a leaf axis is seen in FIG. 4 at 234 with respect to leaf 228. Axis 234 extends to a tip region, for instance, that shown at 236 with respect to leaf 228. Looking additionally to FIG. 6A, tip region 236 of leaf 228 reappears at the noted stage of fabrication. Tip region 236 extends to a forward edge 238 which is seen to taper or slant inwardly toward the base portion 222 from a location of adjacency at tube 240 with the eyelet edge 242 of an eyelet structure represented in general at 244. Eyelet structure 244a is seen to be formed having a cable-receiving aperture 246a, as well as a cable tie-off aperture 248a positioned inwardly therefrom. Eyelet structure 244a extends in a widthwise sense from eyelet edge 242 to an oppositely disposed eyelet edge 252 to define a substantially constant width, W, as identified in FIG. 6C. Edge 252 is seen to be aligned and configured as an extension of leaf side edge 254. Edge 254 is spaced from opposite leaf side edge 256 to define a leaf width. Note additionally, the presence of a centrally disposed chemically milled groove 258. Milled grooves on individual leafs are labeled in FIG. 5 as 258a–258e.

FIGS. 6B and 6C reveal that leaf 228 is configured having a thickness, T, extending between its oppositely disposed leaf faces 260 and 262 (FIG. 6C). As a subsequent step in fabrication, the eyelet structure 244a is seen to be twisted such that its surfaces are substantially perpendicular to leaf faces 260 and 262. Note in FIG. 6B that this twisting incorporates a portion of the leaf tip region 236 to achieve structural buttressing. FIG. 6C further reveals that the eyelet edges 242 and 252 are parallel with the planes represented by leaf face 260 and 262, leaf edge 242 extending below the plane of leaf face 262. With the eyelet structure 244a, the capture component 220 enjoys the capacity to perform within very dense tissue without structural misalignment of the eyelet structures. For a further analysis of such diminutive but robust eyelet structures, reference is made to co-pending application for United States patent by Eggers, et al., entitled Minimally Invasive Instrumentation For Recovering Tissue, filed of even date herewith and having Ser. No. 10/630,488.

Returning to FIG. 5, the cable guide retaining grooves are identified at 258a–258e with respect to leafs 228–232. For the instant embodiment, these grooves 258a–258e function to aid in the support of a flexible polyimide guide tube which serves as a cable guide channel extending centrally along the lengthwise extent of the leafs to terminate in a guide outlet located along each leaf axis and spaced inwardly from the leaf edges, for instance as at 238. This geometry facilitates the dynamic passage of pursing cables from the guide outlet and thence through the cable receiving apertures as at 246*a* (FIGS. 6A, 6C). These guide tubes, which are illustrated in connection with FIG. 5, are quite small having, for example, an outside diameter of about 0.020 inch and a wall thickness of about 0.0015 inch. Such guide tubes are shown in the figure at 268–272 as being adhesively attached to leaf grooves 258*a*–258*e*. Each of the guide tubes 268–272 slidably guides a pursing cable as shown respectively at 278–282. These nineteen-strand cables are formed of a type 316 stainless steel and exhibit when combined or braided, a nominal diameter of about 0.006 inch. The corresponding strand diameters will be about 1.2 mils for that cable diameter. This sizing of the cables is determined with respect to maintaining requisite strengths at electrosurgical excitation temperatures which have been computationally determined to range from about 1400° F. to about 1600° F. The cable components further must retain a capability for readily "playing out" or passing through the cable receiving apertures of the eyelet structures during the initial phase of target tissue capture and, in effect, reversing under stress during the final interval of capture. A detailed discourse concerning the somewhat stringent criteria operationally imposed upon the cables is set forth in the above-identified application for U.S. patent Ser. No. (10/630,488). Polyimide guide tube 268–272 are attached to the chemically etched grooves 258*a*–258*e* within the leafs by initially adhesively coupling them to the grooves. Then, each tube is fixed to a corresponding leaf within the chemically milled groove utilizing an electrically insulative coating material and process which achieves bonding and provides requisite electrical insulation for the entire capture component.

Looking to FIG. 7, that insulative coating is shown at 284 in connection with a sectional view of leaf 228 and associated polyimide tube 268. Coating 284, which has a thickness of about 0.001 inch, is a vapor phase polymerized conformal coating marketed under the trade designation "parylene". Parylene is the generic name for members of a polymer series. The basic member of the series, called parylene C is a poly-para-xylene, a completely linear, highly crystalline material. Such coatings are available from Parylene Coating Service Companies such as Specialty Coating Systems, of Indianapolis, Ind. Other guide tube channel structures may be provided, for example, an extruded polytetrafluoroethylene (Teflon) sheath incorporating a cable guide channel may be secured over thin stainless steel leaf structures. Leafs 228–232 are formed having a thickness, T, preferably of 0.003 inch and a widthwise extent, for example, between leaf side edges 254 and 256 of 0.080 inch. However, the noted thickness may range from about 0.0025 inch to 0.005 inch.

Referring to FIG. 8, a sectional illustration of the forward region 34 and tip 36 of the cannula assembly 22 is provided. Tip 36 is depicted as it is utilized for capturing tissue volumes having a principal effective diametric extent of, for example, extending from about 10 mm to about 20 mm. For larger effective diameter capture specimens, the electrodes will have a lengthier extent. The tip 36 incorporates four precursor electrode components arranged in quadrature or cross-shaped symmetrically about instrument axis 24. Three of the elongate generally L-shape precursor electrodes are revealed at 290–292. When electrosurgically excited, the forward surfaces of the stainless steel wire electrodes function to support a cutting arc. Those forward precursor electrode components are, in turn, located just forwardly of the truncated cone-shaped protective tip 216. Their excitation is carried out by, for example, depression of footswitch 98*a*, or button switch 63, the forward surfaces of the stainless steel wire electrodes function to support a cutting arc. When so excited, the precursor electrodes permit a facile positioning of the forward region 34 of tip 36 into confronting adjacency with a target tissue volume. The forward precursor electrode components are, in turn, located just forwardly of the truncated cone-shaped protective tip 216. Mounted rearwardly of the tip component 216 are polymeric tip components 294 and 296, these components functioning to provide a ramp structure through which the leafs of the capture component 220 may extend. In this regard, leaf 228 with its associated eyelet structure 244*a* is seen in its retracted position. When urged forwardly by the above-noted drive tube 224, these leafs will slidably extend forwardly at an attack angle of about 450. In earlier versions of instrument 12, that extension from the initial position shown at the initial attack angle persisted until the leaf tip regions reached a location corresponding with a maximum effective diametric extent which developed at an intermediate position about one half way along the longitudinal travel of the leafs. At that juncture the pursing cables were abruptly loaded in tension and a rapid pursing activity ensued drawing the leaf tip regions into mutual convergence at axis 24. This earlier locus schematically represented in the figure at 298 as extending about a symbolic target tissue volume 300. However, particularly with configurations for recovering targets with a larger diametric extent in very dense tissue, forces involved tended to cause the output current of motor 186 to elevate in amplitude to undesirable levels which could invoke a capture complete signal prior to achieving full pursing activity and the attainment of a capture position of the leafs. Under the precepts of the instant invention, a gradually increasing cable tension is applied to commence pursing activity somewhat earlier and causing a corresponding gradual altering of the angles of attack to avoid excessive tissue related transverse forces asserted by pursing from adjacent tissue. The result is an altered locus or profile of cutting movement schematically represented at dashed line 302. With both the earlier and the new approach, the volume encapsulated by capture component 220 defines a tissue recovery cage exhibiting an aspect ratio of the maximum effective diametric extent to its length along the longitudinal axis 24 of from about 1:1 to about 1:1.5. The term "effective" is employed with the maximum diametric extent terminology inasmuch as the resultant tissue recovery cage exhibits a generally pentagonal cross-section perpendicular to axis 24.

The structure of the cannula assembly 22 looking inboard from cannula component 32 at forward region 34 is seen to include capture component leafs, two of which are represented at 228 and 231. Next inwardly inboard is a stainless steel support tube 304 which is mounted at the rear portion of support housing 130 of disposable component 16 and extends forwardly through cannula component 32 to a flared region 306 engaging polymeric tip component 294. This flaring is found to be helpful in permitting the support tube to overcome the rather substantial forwardly directed forces occurring during forward deployment of the capture component leafs and cables. Note additionally, that the somewhat annular space between the wall of cannula component 32 and the support tube 304 provides the earlier-noted evacuation system transfer channel diverting elevated temperature fluid. That transfer channel is represented at 308. Channel 308 extends from the intake ports 38 at forward region 34 to suction manifold 28 and its associated evacuation outlet 170 (FIG. 2).

Located inside support tube 304 is an electrosurgical precursor electrode tube 310 which also extends to the rearward portion of support housing 130 for purposes of both support and receiving electrosurgical cutting energy transmitted through electrical contact 144 (FIG. 2). As the precursor electrode tube 310 extends rearwardly, it is electrically insulated from support tube 304 by a polymeric (polyolefin) shrink-wrap 312.

The precursor electrodes are mounted as a subassembly of four stainless steel electrode wires having the noted generally elongate L-shape as seen, in particular, at 290 and 291 in the instant figure. Elongate components of the precursor electrodes, for example as identified at 314 and 316 with respect to electrodes 290 and 291, extend into a subassembly tube 318. Four such electrode assemblies are crimped inside of this tube 318 and that too, in turn, is crimped within the forward portion of the precursor electrode tube 310.

Figure 9:
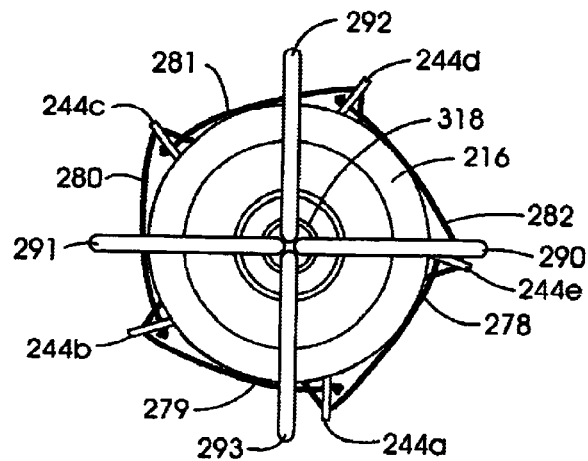
FIG. 9 is a front view of an instrument according to the invention showing a capture component in a retracted orientation.
Figure 10:
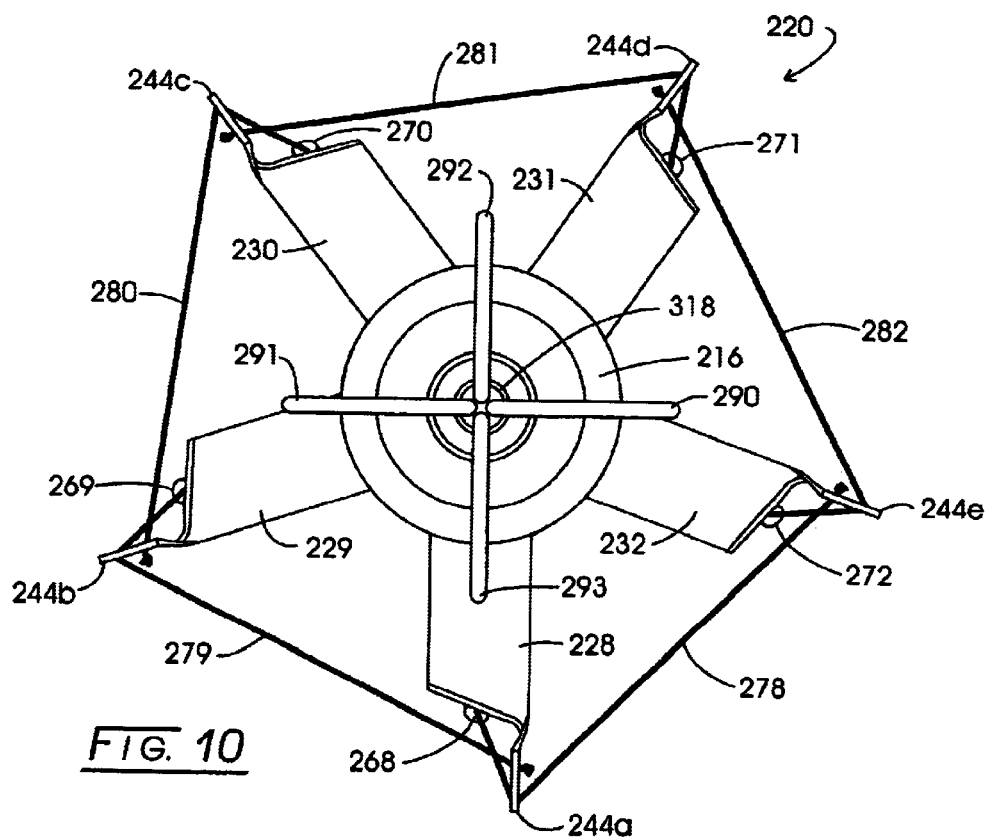
FIG. 10 is a front view of the instrument of FIG. 9 showing the capture component thereof at a stage in its deployment.

Referring to FIGS. 9 and 10, frontal views of the precursor electrodes 290–293 are revealed. In general, the precursor electrodes 290–293 will have a tissue cutting and confronting length of about 6.5 mm to about 7.0 mm for employment with instruments configured to develop a maximum effective capture diameter for the capture component 220 of about 10 mm to about 20 mm. Where that maximum effective diameter expands above about 20 mm up to about 40 mm the corresponding expanse of the precursor electrodes or their lengthwise confronting extent will be about 10 mm to about 15 mm. When configured having one of the larger lengthwise extents, the electrodes are slightly canted forwardly and are made resilient so as to be capable of flexing forwardly as the electrosurgically excited pursing cables physically contact the precursor electrodes. During this procedure, the precursor electrodes are open-circuited and permitted to be re-energized as they are urged into alignment with the capture component leafs. This temporary re-energization of the longer precursor electrodes is found to be beneficial as the electrodes retract or bend toward the target tissue sample being captured.

FIGS. 9 and 10 additionally present front views of the cannula assembly 22 forward region further illustrating the capture component 220 leaf, cabling, and eyelet structures. In this regard, those cables and leafs are illustrated in a retracted state or initial position in FIG. 9, eyelet structure 244a reappearing from FIGS. 6B and 6C and the remaining eyelet structures as being identified at 244b–244e. In contrast, FIG. 10 reveals that orientation of the leafs and cables as they are being deployed toward their maximum diametric extent. Note in that figure that cable 278 emerges from guide tube 268 to pass through the cable-receiving aperture of eyelet structure 244a and extends to a knotted connection with eyelet structure 244e of leaf 232. Similarly, cable 279 extends from guide tube 269, passes through eyelet structure 244b and is tied-off at eyelet structure 244a. Cable 280 emerges from guide tube 270 at leaf 230, extends through eyelet structure 244c and is tied-off at eyelet structure 244b. Cable 281 emerges from guide tube 271, extends through the cable receiving aperture 246d of eyelet structure 244d and is tied-off at eyelet structure 244c. Lastly, cable 282 emerges from guide tube 272 at leaf 232, passes through the cable-receiving aperture of eyelet structure 244e and is tied-off at eyelet structure 244d.

FIG. 10 depicts the capture component 220 at an intermediate position wherein it is at the halfway point along its forwardly directed locus of travel. As it moves from the initial position of FIG. 9 toward this position in the procedure, the pursing cables will have been played out from the guide outlets of the guide tubes and through an associated cable-receiving aperture at an eyelet structure. The geometric relationship between the guide outlet and that aperture is important to facilitate this cable movement. As the cables are progressively loaded in tension approaching this intermediate orientation the leaf tip forward regions will correspondingly assume progressively shallower angles of attack to facilitate leaf movement through very dense tissue. Upon reaching this intermediate position full pursing loads are invoked to effect a rapid convergence of the eyelet structures 244a–244e into mutual adjacency at axis 24. Such full pursing loads advantageously cause a rapid convergence and development of the above-noted desired aspect ratios of the resultant tissue recovery cage substantially encapsulating the tissue volume to be recovered.

In general, within about three seconds following the commencement of the electrosurgical cutting procedure with either the precursor electrodes or the capture component, heat released, for example, from the arc generated steam which condenses within the transfer channel 308 will result in a latent heat of vaporization within that channel which will, in turn, elevate the temperature of the external surface of the wall of cannula component 32. Returning to FIG. 8, this surface heat phenomenon is seen to be accommodated for utilization of a thermally insulative sheath represented generally at 320. Sheath 320 is configured as a stainless steel tube or cylinder 322 having forward and rearward standoffs which are configured by rolling the cylindrical end of the tube 322. The forward standoff is shown at 324. With this construction, an annular air gap or layer 326 is defined which provides thermal insulation. The figure further reveals that extending over the cannula component assembly 22 is an electrically insulative polyolefin shrink-wrap or shrink tube 328. Polyolefin wrap 328 has a thickness of about 0.003 inch. Note that it extends to a forward terminus 330. The gap provided at air layer 326 by the tube 322 is about a 0.017 inch annulus-shaped spacing.

Figure 11:
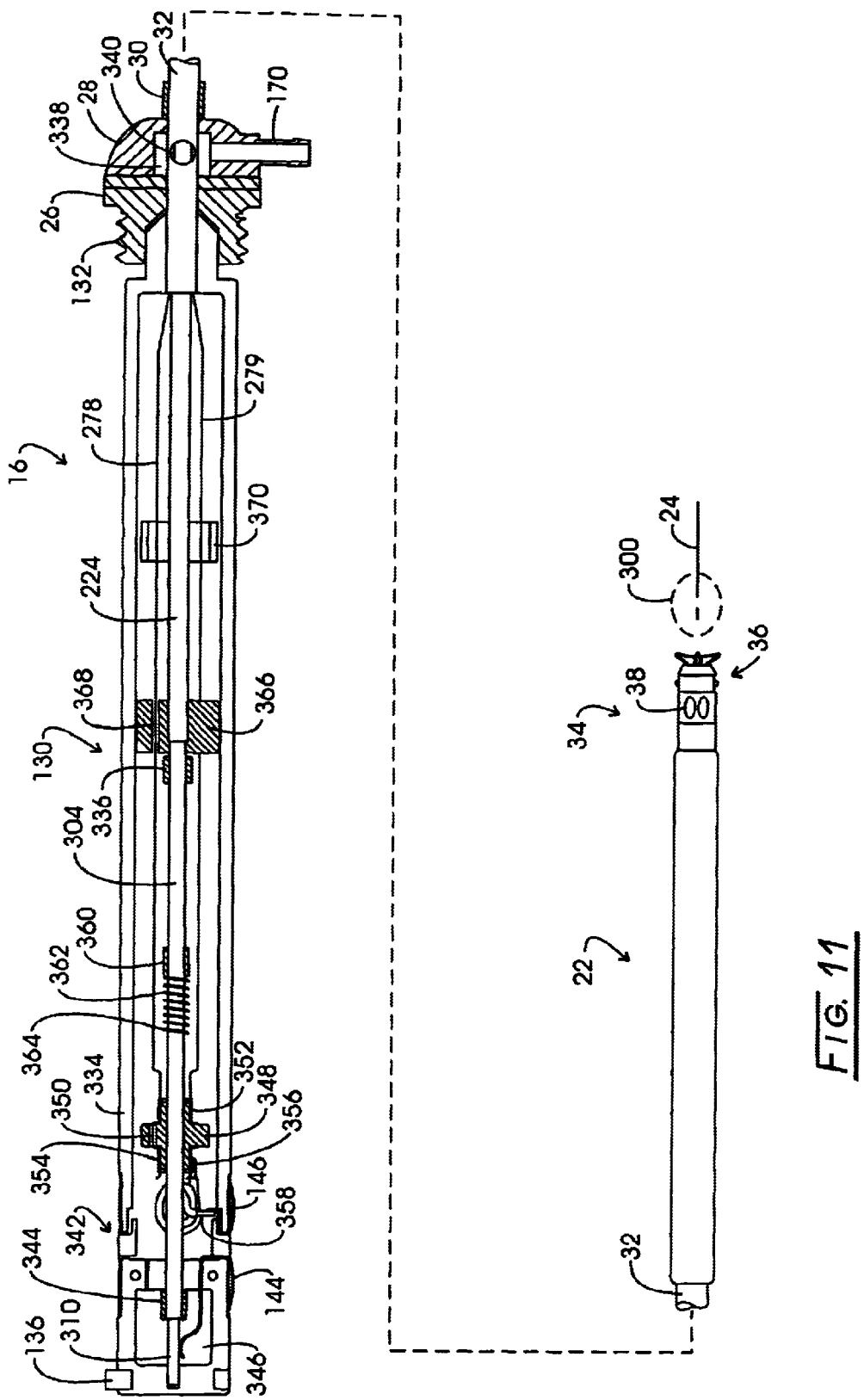
FIG. 11 is a partial sectional view of the disposable component of the instrument shown in FIG. 2 schematically showing the orientation of its components prior to the deployment of a capture component.
Figure 13:
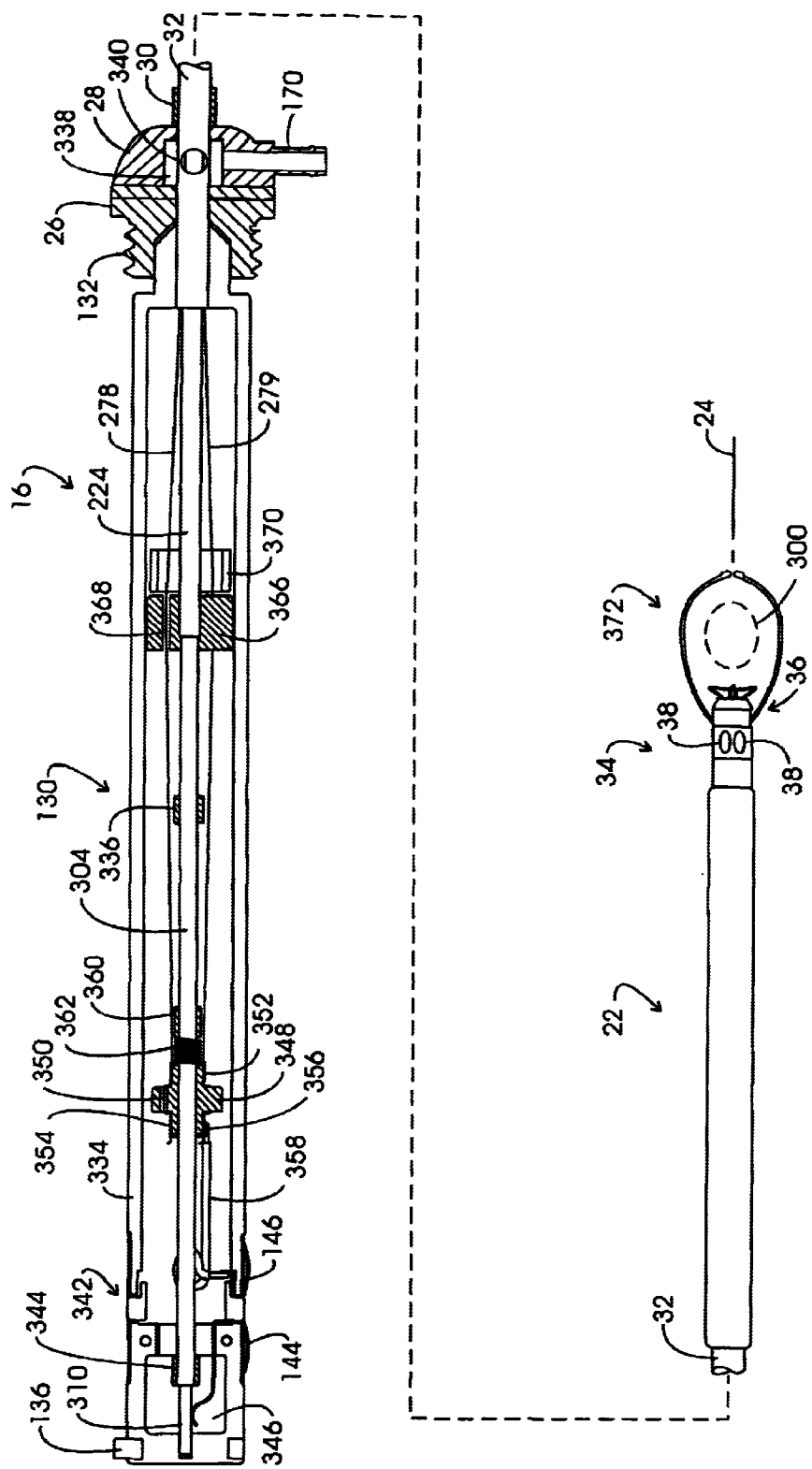
FIG. 13 is a partial sectional view of the instrument of FIG. 11 showing the orientation of the capture component leafs and associated drive features at a completion of capture of a tissue volume.

FIGS. 11–13 provide partial sectional and exploded views of the disposable component 16 as it is positioned in confronting relationship with a target tissue volume 300 at three stages in a specimen retrieval procedure. Looking to FIG. 11, the initial stage in the procedure is represented wherein tip 36 is in confronting relationship with the symbolic target tissue volume 300. In this orientation, capture component 220 will be in the initial position described in connection with FIG. 9. Support housing 130 shows it is formed from two identical moldings one being shown at 334. These paired moldings are retained together adhesively as well as forwardly by connector 26 which, additionally, supports cannula component 32. Component 32 extends through an evacuation chamber 338 formed within manifold 28. Vacuum communication with the chamber 338 is provided by a port or opening 340 in component 32.

Extending from adhesive attachment at a rearward bulk head represented generally at 342 defined by the paired molding components is the inward portion of the earlier-described support tube 304. Tube 304 additionally is anchored at the rearward side of bulkhead 342 by a plastic collar 344. Extending through the interior of the support tube 304 is the earlier-described precursor electrode tube 310, the rear tip of which extends along axis 24 into engagement with the paired molding components 334 and 336 at a cavity 346. That portion of the precursor electrode tube 310 which extends rearwardly from support tube 304 is configured with an electrically conductive surface which receives electrical precursor electrode current through resiliently biased terminal component 144. The remainder of the precursor electrode tube 310, as it extends within support tube 304 is covered with electrically insulative shrink-wrap 312 (FIG. 8). The five, nineteen-strand braided stainless steel cables 278–282 (FIG. 9) extend from their connection with the capture component 220 to a polymeric cable terminator component 348 which is slidably mounted over support tube 304 and moveable thereon in parallel with the instrument axis 24. Two of the braided pursing cables are stylisticly represented in the drawing at 278 and 279. However, all five of these cables extend to and are connected with the cable terminator component 348. Component 348 is formed with five longitudinally disposed and radially spaced channels into each of which one of the cables 278–282 extend. In FIG. 11, cable 278 is seen extending through a channel 350. All five cables are retained or fixed to the terminator component 348 by two stainless steel collars. In this regard, a forward stainless steel collar or ferule is shown at 352 while a rearward one is shown at 354. Collar 354 additionally functions to apply electrosurgical cutting power or current simultaneously to all five of the pursing cables and, accordingly, it initially is nickel plated and then gold plated such that electrosurgical cutting current may be applied to it through a solder union 356. Union 356 connects the collar 354 with a multi-strand and highly flexible insulated copper cable 358. Cable 358, in turn, is soldered (or welded) to the forward electrical terminal assembly 146. Terminator component 348 is stabilized for slidable movement by two outwardly extended guide tabs or ears, one of which has been described at 148 in conjunction with slot 152 in FIGS. 2 and 3. With this arrangement, as the five cables are electrically excited with electrosurgical cutting current, they are drawn in tension forwardly to, in turn, pull the terminator component 348 in slidable fashion forwardly over the support tube 304. This sliding movement under the drive of cable tension continues until the cable terminator component 348 encounters a cable stop 360 which is fixed to support tube 304 at a location which is selected to establish the maximum effective diametric extent of opening and overall length of the containment structure or cage generated by the capture component 220. This is the only adjustment required for developing a variation in such effective diametric extent and length dimensioning. In this regard, that effective diametric extent may range from about 10 mm to about 40 mm.

In general, cable stop collar 360 is located such that the sliding movement of terminator component 348 is blocked when capture component 220 achieves the intermediate position generally representing one half of its longitudinal deployment and a maximum effective diametric extent. The capturing performance of instrument 12 may be importantly improved such that its use may extend to the recovery of very dense tissue by deriving a pursing stress on the cables which progressively increases toward a higher value generally established by blockage at cable stop 360. This progressive cable loading occurs as terminator component 348 approaches stop 360 and is implemented by the positioning of a resilient component present as a compression spring 362 located in abutment with cable stop collar 360. Note that the spring 362 extends rearwardly from its abutting engagement with stop 360 to a location identified at 364. With the arrangement, helical compression spring 362 functions to modulate the extent of tension applied to the cables such that the leaf tip regions as described in conjunction with FIGS. 6A–6C are more gradually vectored inwardly toward axis 24 at the commencement of pursing activity to accommodate for the interposition of spring 362 between terminator component 348 and collar 360, the latter component is moved forwardly by an amount corresponding with the bottomed-out or solid height of a fully compressed spring 362. For performance in conjunction with capture configurations of from about 10 mm to about 15 mm maximum effective diametric extent, spring 362 will have a length of about 0.25 inch, a solid height of about 0.1 inch and a spring rate of about 7 to 10 pounds per inch. The spring height extending to location 364 provides for the commencement of compressive application of pursing loads upon the cables when capture component 220 will have moved longitudinally about 75% to about 90% of the distance otherwise deriving an intermediate position representing an opening of effective diametric extent. Skilled artisans will recognize that the configuration of the spring of the invention can be modified for specific applications, for spring length and solid height; spring constant; or alternatively by utilizing a varying rate spring.

Drive imparted to capture component 220 is developed from drive tube 224 which, as described in connection with FIG. 3 is, in turn, driven from its outwardly disposed drive ears or tabs 160 and 162 which extend through slots, one of which is shown at 156 in FIG. 3. The drive member associated with these tab is shown in FIG. 11 at 366 in its initial or home orientation. Member 366 is attached to drive tube 224 which is slidably mounted over support tube 304 and extends forwardly through the cannula component 32 into welded engagement with the pentagonal base portion 222 of capture component 220 (FIG. 4). A drive member 366 is driven forwardly, the five pursing cables 278–282 pass through it via five channels. One such channel is stylistically represented in the figure at 368 in conjunction with representative cable 278. Drive tube 224 as well as cables 278–282 additionally slide over a capture stop component 370 which is mounted to the housing 130 paired components. Stop 370 is fixed in place in conjunction with earlier-described tab 172 (FIG. 2). The drive member 366 eventually will closely approach or engage the stop component 370 at the completion of pursing down with attendant derivation of a stall-induced spike at motor 186 (FIG. 3). With the arrangement, the stop component 370 additionally functions as a safety stop assuring the limited travel of drive member 366. As drive member 366 and cable driven terminator component 348 are driven forwardly, spring 362 is initially engaged at location 364 and generally, will fully compress the spring against cable stop 360 to define an intermediate position. Looking to FIG. 12, this intermediate position is revealed. The symbolically depicted leafs of capture component 220 are shown defining a maximum effective diametric extent. Spring 362 is shown fully compressed defining its solid height, which for the instant embodiment will be about 0.1 inch. Note, additionally, that the symbolically depicted leafs of capture component 220 will have emerged at the initial attack angle of about 45°, whereupon such attack angle is modulated inwardly toward axis 24 by the gradual loading of cables 278–282 in tension. Note, additionally, that at this intermediate position of the attack angle of the forward regions of the capture component leafs will reside in planes somewhat parallel with axis 24. More rapid or full pursing of the pursing cables 278–282 now ensues. The pursing value tensile stress asserted at the cables functions to derive a rapid purse down activity. That rapid purse down also is facilitated by the pursing cable assemblage providing a discrete cable for each of the five leafs. This advantageously minimizes the lengthwise extent of the resultant tissue recovery cage 372. Looking to FIG. 13, the capture component, as schematically represented at 220, has completed enclosure of the capture basket configuration of tissue recovery cage 372. Note in the figure that terminator component 348 remains in compressive contact with spring 362 and cable stop 360 and that drive member 366 has moved into somewhat close adjacency with stop member 370. Just as this orientation is reached, motor 186 (FIG. 3) will stall to provide a procedure termination signal which is recognized at control assembly 70 and the application of electrosurgical cutting current to pursing cables 278–282 is terminated. A stop component 336 also is fixed to support tube 304 behind drive member 366. This component limits the return movement of member 366 during post fabrication testing.

Figure 14:
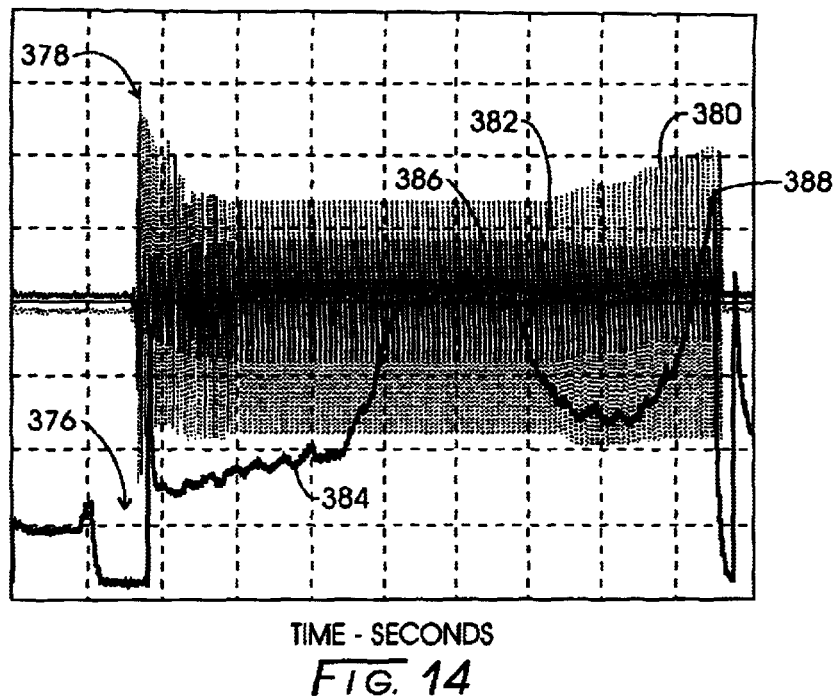
FIG. 14 is a representation of an oscillitrace showing motor performance in conjunction with electrosurgical cutting voltage and current of one version of the instrument shown in FIG. 2 for a 10 mm capture.

As noted earlier herein, the utilization of resilient member such as spring 362 in conjunction with cable terminator component 348 and cable stop 360 facilitates the use of instrument 12 in recovering specimens from very dense tissue. That tissue has been somewhat replicated through the utilization of mechanically compressed porcine breast tissue. Referring to FIG. 14, an oscillitrace is represented wherein a sample of the noted porcine tissue was recovered utilizing an instrument configuration deriving a sample having a maximum effective diametric extent of about 10 mm. The instrument was utilized in conjunction with a Model 3000 RF controller marketed by Neothermia Corporation (supra). In the figure, the procedure is represented as extending from left to right with each of the vertical time divisions representing one second. Commencement of electrosurgical cutting is represented at 378. Cutting voltage applied to the pursing cables is represented at 380 and corresponding cutting current is represented at 382. Curve 384 corresponds with motor drive current. The region of motor current curve 384 extending before the commencement of curves 380 and 382 represents an initial motorization test following turn-on wherein yoke 210 is driven into contact with tabs 160 and 162 (FIG. 3) whereupon the motor is de-energized at motor current excursion 376 and then re-energized to commence the procedure at 378. Note that following about three seconds after excitation of power to the pursing cables at 378 within the procedure, the motor drive current elevates substantially, reaching a high point of about 109 milliamps at peak 386. The higher mode of current values represented, for example, at 386 were deemed undesirable. At the termination of the procedure with full pursing down of the cables a motor stall condition is recognized as being above 130 milliamps as seen at the current excursion 388. As is evident from the oscillitrace, at that point in the procedure, cutting energy was terminated.

Figure 15:
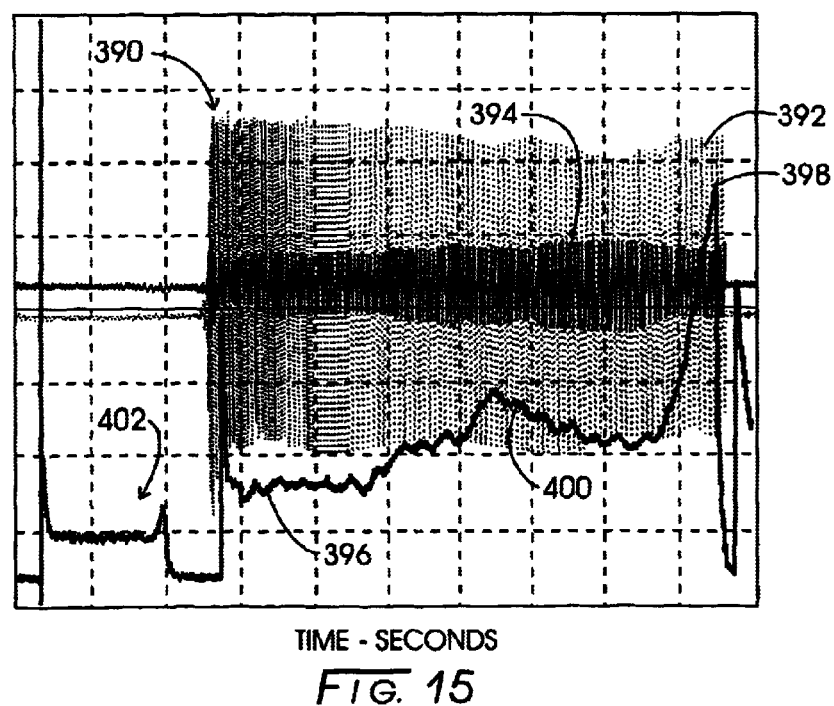
FIG. 15 is a representation of an oscillitrace showing motor performance in conjunction with electrosurgical cutting voltage and current in conjunction with motor current of an alternative version of the instrument shown in FIG. 2 for a 10 mm capture.

The test represented at FIG. 14 was repeated, again with an instrument configuration for recovering a sample having about a 10 mm maximum effective diametric extent and utilizing compressed porcine breast tissue. Referring to FIG. 15, the test was repeated with an instrument employing a spring as at 362. The spring had a length of 0.25 inch and a spring rate of 7.5 pounds per inch. As before, in the figure the procedure is considered to extend from left to right and its approximate seven second duration is represented by one second duration vertical divisions. For this test, cutting voltage at the pursing cables is represented at 392 while corresponding cutting current is represented at 394. Motor drive current is represented at 396. Note that following about three seconds at which time the spring will have been fully compressed, motor current reaches a peak of only about 60 milliamps as represented at location 400. As before, at full pursing and motor stall the stall current spike at 398 was recognized by the controller and energization of the pursing cables was terminated. The minimal current excursion represented at location 400 represents safe and desirable performance within very dense tissue. As in the case of FIG. 14, the configuration of motor drive current trace 396 at 402 prior to the commencement of curves 392 and 394 at 390 is involved with an initial motor test prior to turn-on commencing the procedure.

Figure 16:
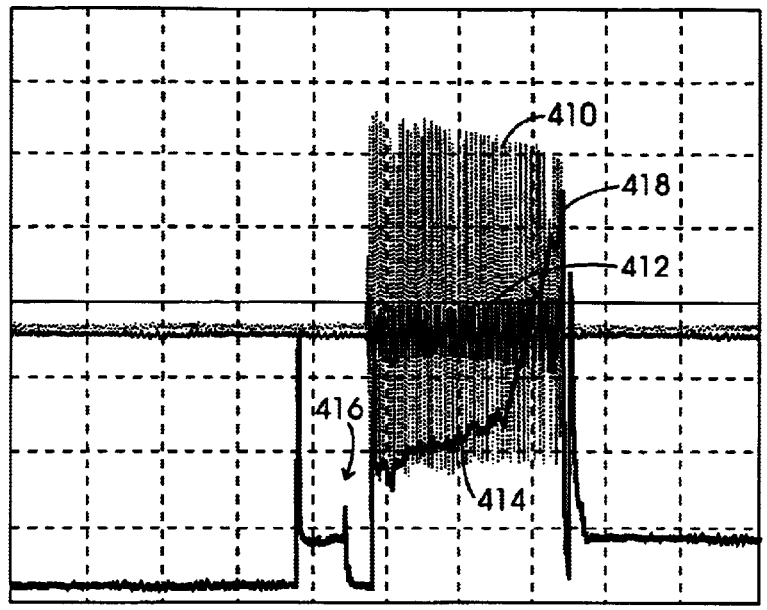
FIG. 16 is a representation of an oscillitrace for a 20 mm maximum effective capture diameter showing motor current evidencing a premature stall in conjunction with electrosurgical cutting voltage and current.

Tests were also carried out utilizing compressed porcine breast tissue to emulate very dense human tissue in conjunction with recovery of a tissue specimen having a maximum effective diameter of about 20 mm. For these tests, the cable stop 360 was positioned forwardly for the 20 mm effective diametric sizing and in conjunction with utilization of a spring. In one test, when using a spring having a length of 0.25 inch and a spring rate or spring constant of 7.5 pounds per inch, the test resulted in a stall failure. Referring to FIG. 16, an oscillitrace corresponding with this test is presented. In the figure, the procedure is considered to progress in time from left to right. For this demonstration, the vertical time divisions represent two second increments. Cutting voltage applied to the precursor cables is represented at trace 410. Corresponding cutting current applied to the pursing cable is represented at trace 412 and trace 414 corresponds with motor current. Following motor initial test procedures represented at curve 414 at region 416, note that at about three and one half to four seconds following the commencement of the procedure motor current rose abruptly as represented at region 418, whereupon a stall condition ensued.

Figure 17:
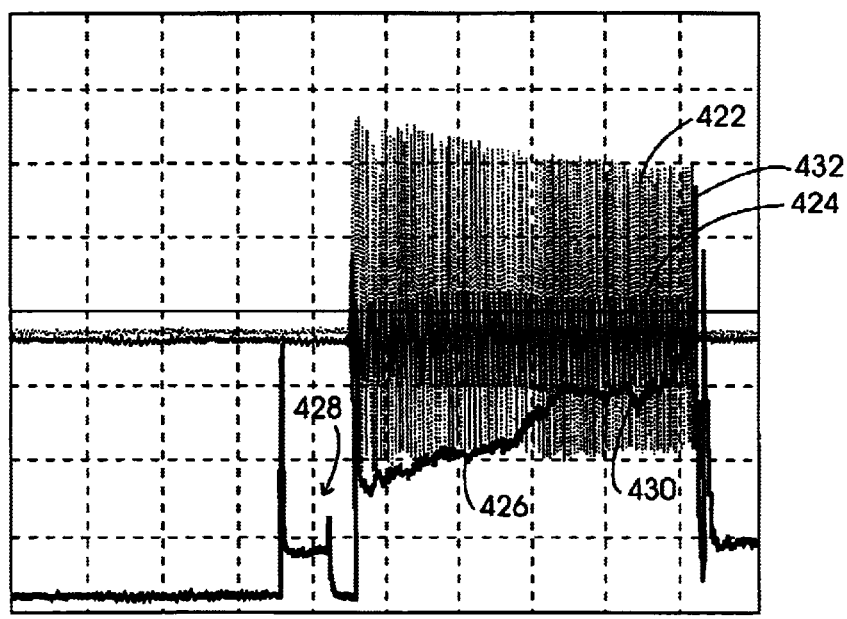
FIG. 17 is a representation of an oscillitrace showing a recovery of a tissue sample of 20 mm effective diameter, showing motor current in combination with electrosurgical cutting voltage and current.

Referring to FIG. 17, an oscillitrace is represented corresponding with a configuration of instrument 12 for establishing a maximum effective sample diameter of about 20 mm. For this test, two compression springs, each having a free length of 0.250 inch and a spring rate or constant of 7.50 pounds per inch were employed in tandem. Thus, the effective additive spring length was 0.500 inch and the resultant spring force constant was reduced to 3.75 pounds per inch. Cable stop 360 was located accordingly for above the anticipated specimen effective diametric extent and the increased solid height of the tandem compression springs when fully compressed. As in FIG. 16, the oscillitrace represented at FIG. 17 is arranged with vertical divisions representing two seconds. Cutting voltage applied to the pursing cables is represented at 422. Cutting current applied to the pursing cables is represented at trace 424 and trace 426 corresponds with motor drive current. Following initial motor testing as represented at region 428 of curve 426, the procedure commenced and full capture was achieved. In this regard, motor current following the leafs attaining intermediate position as represented at region 430 of curve 426 was at satisfactory lower levels. Motor stall at the completion of capture and full pursing of the capture component leafs is represented at sharp transition or spike 432. Such capture also will be successful for this designated maximum effective diametric extent where a single spring having a length of 0.25 inch and a spring force constant or spring rate of 10 to 15 pounds per inch is employed.

Figure 18:
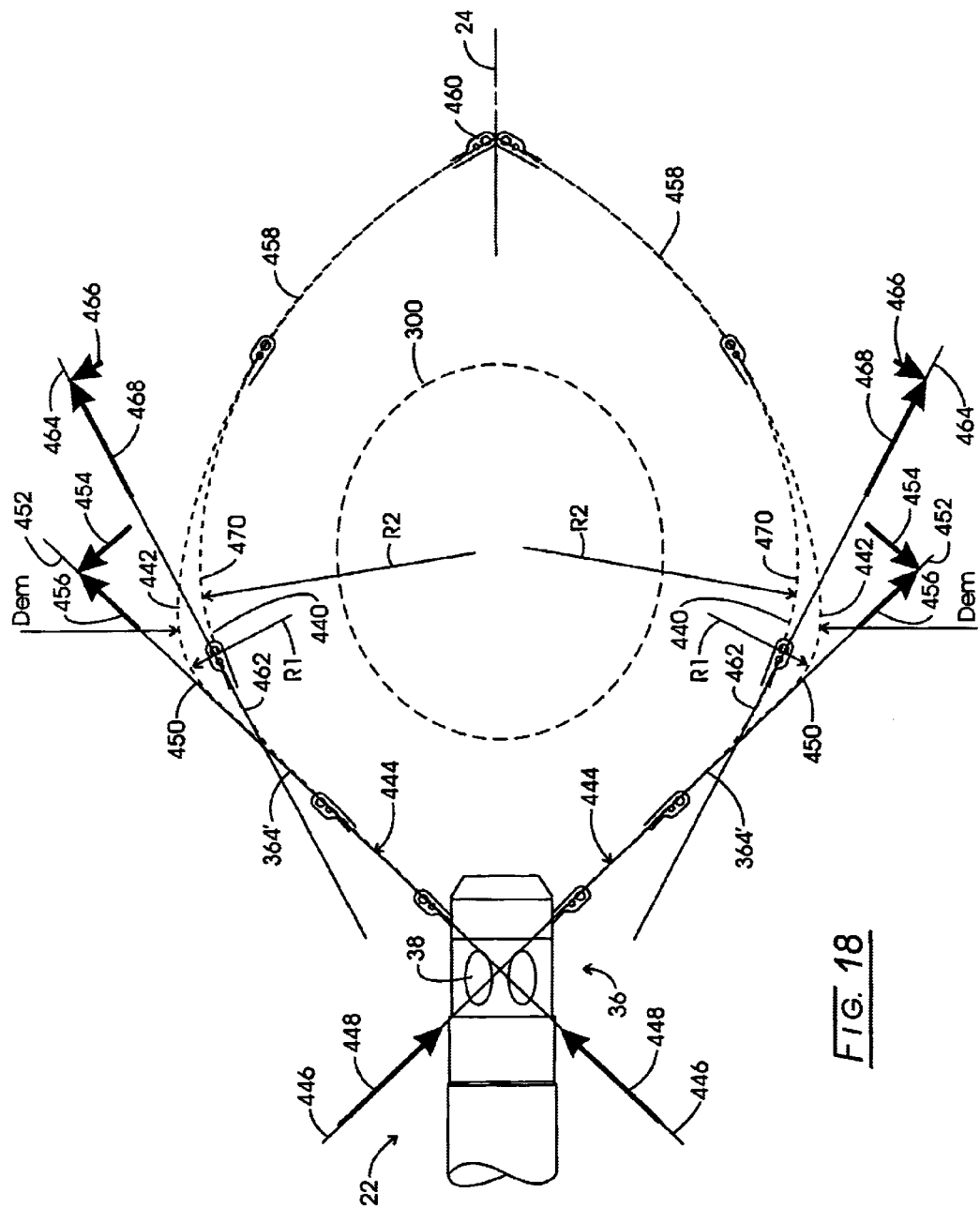
FIG. 18 is a schematic representation of a capture component cutting profile without and with the modulated pre-tensioning feature of the invention.

Referring to FIG. 18, the tip region 236 of cannula assembly 22 is schematically illustrated in association with loci of travel of the leading or cutting edges and leaf tip regions of capture component 220. These loci are plotted to represent the capture component leading edge without the influence of modulated pre-tensioning derived by springs at 362 and with their presence. The loci further are illustrated in conjunction with tangent lines and radii of curvature to those tangent lines. In the figure, the locus of travel of the cables and associated tip regions implemented with the spring is shown at dashed line 440, while the locus of cutting travel without such pre-tensioning modulation is shown at dashed line 442.

As the capture component leafs are deployed from their initial or retracted position, their leaf tip regions assume an initial angle of attack which will be in the range of from about 35° to about 45° with respect to axis 24. Until spring contact location 364 (FIG. 11) is reached, the two loci will be coincident. This region of coincidence is shown in general at 444 in conjunction with similarly coincident tangent lines 446. During this initial emergence, the leaf tip regions are aligned with tangents 444 and thus are straight and in a compressive state with dismissible lateral forces imposed by the tissue through which they are extending. This structural condition may be represented by elongate singular vectors 448. Such coincidence continues until the noted location of spring contact is reached. That location is shown with the same numeration but in primed fashion at 364' in the figure. Without pre-tension modulation effected by the spring, locus 442 is seen to extend to region 450 at which position terminator component 348 will have contacted cable stop 360 (FIG. 12) in sudden fashion without the intervention of spring 362. A tangent to this condition at locus 442 is represented at 452 in conjunction with a corresponding radius of curvature R1. Due to the abruptness of the imposition of pursing tension curvature radius R1 is somewhat short. Another result, particularly where very dense tissue is involved is the imposition of tissue imposed side loads shown at vector 454 with a diminution of the extent of more forwardly directed forces as represented at vector 456. A sharp curvature encountered at region 450 further identifies the location of attainment of the noted maximum diametric extent represented in the figure at $D_{em}$. It is at this region 450 that undesirably high motor current conditions may be witnessed where samples are taken from very dense tissue. Upon the locus 442 angle of attack changing to convergence toward axis 24 tissue derived lateral forces tend to diminish and the capture is completed as represented at region 458. In region 458, the loci again become coincident as capture position 460 is approached.

Now considering locus 440 with the spring modulated pre-tensioning of the cable prior to attainment of the intermediate position of maximum effective diametric extent, note that following coincident region 444 contact location 364' is reached to provide for a gradual inwardly directed change of the angle of attack of the leaf tip regions. Commencement of this gradual curvature is identified at region 462 and the associated tangent 464 with radius of curvature R2. That radius of the curvature will be much larger than the radius of curvature R1. Lateral tissue involved vector 466 is now lesser extent while the force vector aligned with the leaf tip regions as at 468 remain at an effective value. Locus 440 then continues until spring 364 is fully compressed at region 470 and ultimately merges into coincidence region 458 and progresses to capture position 460.

Since certain changes may be made in the above-described apparatus and method without departing from the scope of the invention herein involved, it is intended that all matter contained in the description thereof or shown in the accompanying drawings shall be interpreted as illustrative and not in a limiting sense.

What is claimed is:

1. Apparatus for retrieving a tissue volume, comprising:
a delivery member having an interior channel extending from a proximal portion along a longitudinal axis to a forward region having a distal end;
a capture component positioned at said delivery member forward region, having a forward portion extending to a forwardly disposed tip region and pursing cable assembly energizable to define an electrosurgical cutting leading portion, said cable assembly including one or more tensionable cables extending from said forward portion along said interior channel to a cable terminator, said forward portion being drivably extendable from an initial position outwardly from said axis and forwardly at a tip region initial angle of attack toward an intermediate position while drawing said cables forwardly, said electrosurgical cutting leading portion defining a cutting profile of maximum effective diametric extent in correspondence with said intermediate position, and subsequently being drivably extendable while being drawn in contraction toward said axis at tip region inwardly directed full pursing angles of attack by pursing stress at said cable assembly to a capture position; and
a control assembly having a drive portion in driving engagement with said capture component and actuable to drive said capture component forward portion from said initial position into said capture position, said control assembly effecting the electrosurgical energization of said pursing cable assembly, and being configured to effect a loading of said one or more tensionable cables to derive a said pursing stress which progressively increases toward a higher value to establish corresponding tip region transition pursing angles of attack which commence prior to attainment of said intermediate position and prior to commencement of said tip region full pursing angles of attack.

2. The apparatus of claim 1 in which:
said control assembly is configured to effect said loading of said one or more tensionable cables by progressively inhibiting the movement of said cable terminator with said cables when drawn forwardly.

3. The apparatus of claim 1 in which:
said cable terminator is movable forwardly with said cables along a support member;
said control assembly comprises a stop member positioned upon said support member to engage said cable terminator to block the movement thereof, and a resilient component positioned intermediate said stop member and said cable terminator, engagable with said cable terminator to effect said derivation of said pursing stress which progressively increases.

4. The apparatus of claim 3 in which:
said control assembly resilient component comprises one or more springs.

5. The apparatus of claim 4 in which:
said cutting profile maximum effective diametric extent is from about 10 mm to about 15 mm; and
said one or more springs exhibit a spring rate of about 7 to 10 pounds per inch.

6. The apparatus of claim 5 in which:
said one or more springs are compression springs having a length of about 0.25 inch.

7. The apparatus of claim 4 in which:
said cutting profile maximum effective diametric extent is about 20 mm or more; and
said one or more springs exhibit a spring rate of about 10 to 15 pounds per inch.

8. The apparatus of claim 7 in which:
said one or more springs are compression springs having a length of about 0.25 inch.

9. The apparatus of claim 4 in which:
said one or more springs exhibit a spring constant effective to maximize the effective diametric extent of said cutting profile when said capture component forward portion is at or adjacent said intermediate position.

10. The apparatus of claim 9 in which:

said one or more springs are compression springs having a length effective to maximize the effective diametric extent of said cutting profile when said capture component forward portion is at or adjacent said intermediate position.

11. The apparatus of claim 1 in which:

said capture component forward portion is configured to define a tissue recovery cage when said capture position is attained;

said control assembly is configured to derive said pursing stress to define said tissue recovery cage exhibiting an aspect ratio of said maximum effective diametric extent to its length along said longitudinal axis of from about 1:1 to about 1:1.5.

12. The method for isolating and retrieving a tissue volume, comprising the steps of:

(a) providing a delivery member having an interior channel extending from a proximal portion along a longitudinal axis to a forward region having a distal end;

(b) providing a capture component positioned at said delivery member forward region, having a forward portion comprised of a plurality of cable supports having tip portions of given width supporting a forwardly disposed pursing cable assembly including one or more electrically conductive tensionable cables extending from said tip portions along said interior channel and arranged at said tip portions to define an electrosurgical cutting edge, said forward portion having an initial position substantially within said interior channel;

(c) positioning said delivery member at an operative location wherein said distal end is located in adjacency with said tissue volume;

(d) electrosurgically exciting said capture component cables to form a cutting arc at said electrosurgical cutting edge;

(e) driving said capture component from said initial position to effect said deployment of said cable supports at an initial angle of attack and to expansively move said electrosurgical cutting edge toward an intermediate position corresponding with a cutting profile defining a maximum effective diametric extent;

(f) loading said cables with a pursing stress which progressively increases to progressively alter the angle of attack of said cable support tip portions defining a curvature toward said longitudinal axis as said intermediate position is approached to an extent facilitating the forward movement of said cable supports;

(g) loading said cables with a pursing value of tensile stress effective to converge said tip portion to a capture position defining a tissue recovery cage substantially encapsulating said tissue volume;

(h) terminating said electrosurgical excitation; and (i) removing said delivery member forward region from said operative location.

13. The method of claim 12 in which:

said step (f) carries out the loading of said cables to have progressively altered the angle of attack of said tip portion from said initial angle of attack substantially to a parallel orientation with said longitudinal axis at said intermediate position.

14. The method of claim 12 in which:

said step (f) is carried out by spring biasing said cables.

15. The method of claim 14 in which:

said step (e) maximum effective diametric extent is from about 10 mm to about 15 mm; and said spring biasing is carried out at a spring rate of about 7 to 10 pounds per inch.

16. The method of claim 14 in which:

said step (e) maximum effective diametric extent is about 20 mm or more; and said spring biasing is carried out at a spring rate of about 10 to 15 pounds per inch.

17. The method of claim 12 in which:

said step (f) loads said cables in a manner defining a said curvature as having progressively decreasing radii.

18. A system for retrieving a tissue volume, comprising:

a cannula assembly with an interior channel extending from a proximal portion along a longitudinal axis to a forward region;

a capture component positioned at said cannula assembly forward region, having a forward portion with a plurality of cage defining leafs extending to generally flat tip regions configured to mount a pursing cable assembly having a plurality of cables energizable to define an electrosurgical cutting leading edge at said tip regions, said cables extending along said cannula assembly interior channel to a connection with a cable terminator, said capture component being drivable to extend said leafs from an initial position generally within said interior channel at an initial attack angle outwardly and forwardly toward an intermediate orientation corresponding with a maximum effective diameter said cables being loadable in tension to effect a pursing of said leaf tip regions to converge toward said longitudinal axis to exhibit a capture orientation;

a support assembly configured to support said cable terminator for slideable forward movement under drive from said cables;

a drive assembly having a drive member drivably engaged with said capture component and extending to a driven portion and a motor driver assembly energizable to impart drive movement to said driven portion to effect application of drive to said capture component and exhibiting a stall condition upon attainment by said capture component of said capture orientation;

a cable stop located to effect blockage of said slideable forward movement of said cable terminator at a position corresponding substantially with said capture component intermediate orientation;

a pre-tensioning assembly configured to assert a modulated pretension upon said cables at said cable terminator prior to said blockage thereof effective to provide a progressive alteration of said initial attack angle toward said longitudinal axis to inhibit a premature derivation of said stall condition; and a control assembly controllable to effect said energization of said motor driver and said pursing cables, and to de-energize said pursing cables and said motor driver in response to said stall condition.

19. The system of claim 18 in which:

said pre-tensioning assembly comprises a resilient component.

20. The system of claim 19 in which:

said resilient component comprises at least one spring.

21. The system of claim 20 in which:

said at least one spring is a compression spring positioned intermediate to said cable stop and said cable terminator.

22. The system of claim 20 in which:

said maximum effective diameter is from about 10 mm to about 15 mm; and said at least one spring exhibits a spring rate of about 7 to 10 pounds per inch.

23. The system of claim 22 in which:

said at least one spring is a compression spring positioned intermediate to said cable stop and said cable terminator, and has a length of about 0.25 inch.

24. The system of claim 20 in which:

said maximum effective diameter is about 20 mm; and said at least one spring exhibits a spring rate of about 10 to 15 pounds per inch.

25. The system of claim 24 in which:

said at least one spring is a compression spring positioned intermediate to said cable stop and said cable terminator, and has a length of about 0.25 inch.

26. The system of claim 18 in which:

said capture component defines a tissue recovery cage when at said capture orientation; and said pre-tensioning assembly is configured to define said tissue recovery cage as exhibiting an aspect ratio of said maximum effective diameter to its length along said longitudinal axis of from about 1:1 to about 1:1.5.

* * * * *